(12) United States Patent
Moine et al.

(10) Patent No.: US 9,320,806 B2
(45) Date of Patent: Apr. 26, 2016

(54) IMPLANTABLE SWELLABLE BIO-RESORBABLE POLYMER

(75) Inventors: Laurence Moine, Saint Cloud (FR); Alexandre Laurent, Courbevoie (FR); Michel Wassef, Paris (FR); Laurent Bedouet, Paris (FR); Stephanie Louguet, Bordeaux (FR); Valentin Verret, Gentilly (FR); Emeline Servais, Janvry (FR)

(73) Assignees: Occlugel, Jouy en Josas (FR); Centre National De La Recherche Scientifique, Paris (FR); Assistance Publique-Hopitaux De Paris, Paris (FR); Universite Paris Diderot-Paris, Paris (FR)

( * ) Notice: Subject to any disclaimer, the term of this patent is extended or adjusted under 35 U.S.C. 154(b) by 320 days.

(21) Appl. No.: 14/003,514

(22) PCT Filed: Mar. 9, 2012

(86) PCT No.: PCT/EP2012/054177
§ 371 (c)(1),
(2), (4) Date: Sep. 6, 2013

(87) PCT Pub. No.: WO2012/120138
PCT Pub. Date: Sep. 13, 2012

(65) Prior Publication Data
US 2013/0344159 A1 Dec. 26, 2013

Related U.S. Application Data

(60) Provisional application No. 61/450,725, filed on Mar. 9, 2011.

(30) Foreign Application Priority Data

Mar. 9, 2011 (EP) .................................... 11305254

(51) Int. Cl.
| | | |
|---|---|---|
| A61K 47/48 | (2006.01) | |
| A61K 47/34 | (2006.01) | |
| C08F 220/18 | (2006.01) | |
| C08F 222/10 | (2006.01) | |
| C08F 224/00 | (2006.01) | |

(52) U.S. Cl.
CPC ........... *A61K 47/48176* (2013.01); *A61K 47/34* (2013.01); *A61K 47/48192* (2013.01); *C08F 220/18* (2013.01); *C08F 222/1006* (2013.01); *C08F 224/00* (2013.01); *Y10T 428/2982* (2015.01)

(58) Field of Classification Search
CPC ............ A61K 47/34; A61K 47/48176; A61K 47/48192; C08F 220/18; C08F 222/1006; C08F 224/00; Y10T 428/2982
See application file for complete search history.

(56) References Cited

U.S. PATENT DOCUMENTS

2007/0155926 A1   7/2007 Matyjaszewski et al.

FOREIGN PATENT DOCUMENTS

| WO | 2007072481 | | 6/2007 |
| WO | 2009049230 | | 4/2009 |
| WO | 2009132206 | A1 | 10/2009 |
| WO | 2011029867 | | 3/2011 |

OTHER PUBLICATIONS

Yamamoto et al., Efficient Fixation of Carbon Dioxide into Poly(glycidyl methacrylate) Containing Pendant Crown Ether, Macromolecules, vol. 36, pp. 1514-1521, dated 2003.
Tobio et al., Stealth PLA-PEG Nanoparticles as Protein Carriers for Nasal Administration, Pharmaceutical Research, vol. 15, No. 2, pp. 270-275, dated 1998.
Ren et al, Noncovalently Connected Micelles Based on a Beta-Cyclodextrin-Containing Polymer and Adamantane End-Capped Poly(E-caprolactone) via Host-Guest Interactions, Journal of Polymer Science: Part A: Polymer Chemistry, vol. 47, pp. 4267-4278, dated 2009.
Louguet et al., Poly(ethylene glycol) methacrylate hydrolyzable microspheres for transient vascular embolization, Accepted Manuscript, to appear in Acta Biomaterialia, dated 2013.

(Continued)

*Primary Examiner* — Kyle Purdy
(74) *Attorney, Agent, or Firm* — Banner & Witcoff, Ltd.

(57) ABSTRACT

The present invention relates to a polymer obtained from the polymerization of: (i) at least one monomer of formula (I) $(CH_2=CR_1)CO-K$ (1) wherein: —K represents O—Z or NH—Z, Z representing $(CR_2R_3)m-CH_3$, $(CH_2-CH_2-O)m-H$, $(CH_2-CH_2-O)m-CH_3$, $(CH_2)m-NR_4R_5$ with m representing an integer from 1 to 30; —$R_1$, $R_2$, $R_3$, $R_4$ and $R_5$ independently represent H or a C1-C6 alkyl; (ii) at least between 0.1 and 50% mol, advantageously between 1 and 30% mol, more advantageously between 1 and 20 mol % of a cyclic monomer having a exomethylene group of formula (II) wherein: — R6, R7, R8 and R9 represent independently H or a C5-C7 aryl group or R6 and R9 are absent and R7 and R8 form together with the carbon atom on which they are bonded a C5-C7 aryl group; —i and j represent independently an integer chosen between 0 and 2; —X represents either O or X is not present and in this latter case, CR6R7 and CR8R9 are linked via a single bond C—C and (iii) at least one bio-resorbable block copolymer cross-linker.

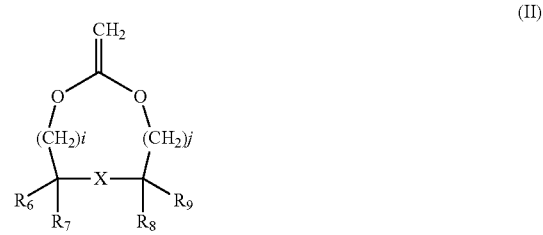

(II)

19 Claims, No Drawings

(56) References Cited

OTHER PUBLICATIONS

International Search Report mailed Apr. 10, 2012, for PCT/EP2012/054177.
Osuga, et al., Transarterial Embolization for Large Hepatocellular Carcinoma with Use of Superabsorbent Polymer Microspheres: Initial Experience, J Vasc Interv Radiol., vol. 13, pp. 929-934. dated 2002.
O'Brien, The effect of pore size on cell adhesion in collagen-GAG scaffolds, Biomaterials, vol. 26, pp. 433-441, dated 2005.
Brown, Solvent/Non-solvent Sintering: A novel Route to Create Porous Microsphere Scaffolds for Tissue Regeneration, J. Biomed Mater Res. B Appl Biomater, vol. 86B(2): pp. 396-406, dated 2008.
Von Heimburg, et al., Human preqadipocytes seeded on freeze-dried collagen scaffolds investigated in vitro and in vivo, Biomaterials, vol. 22, pp. 429-438, dated 2001.
Zeltinger, et al., Effect of Pore Size and Void Fraction on Cellular Adhesion, Proliferation, and Matrix Deposition, Tissue Engineering, vol. 7, No. 5, pp. 557-572, dated Oct. 2001.
Scorah et al., Experimental Study of a Tetrafunctional Peroxide Initiator: Bulk Free Radical Polymerization of Butyl Acrylate and Vinyl Acetate, Polymer Bulletin, vol. 57, pp. 157-167, dated 2006.
Loubat, Telomerization of acrylic acid with mercaptans: Part 2. Kinetics of the synthesis of star-shaped macromolecules of acrylic acid, Polym. Int., vol. 50, pp. 375-380, dated 2001.
Odian, Principles of Polymerization, 3rd ed., J. Wiley, New York, Complete Book Cover to p. 812—(Only Cover and Table of Contents included)—If Examiner requires complete copy, please advise.
Stella, Prodrugs Do They Have Advantages in Clinical Practice?, Drugs, vol. 29, pp. 455-473, dated 1985.
Babazadeh, Synthesis and study of controlled release of ibuprofen from the new acrylic type polymers, Int J Phar, vol. 316, pp. 68-73, dated 2006.
Vlugt-Wensink et al, In Vitro Degradation Behavior of Microspheres Based on Cross-Linked Dextran, Biomacromolecules, vol. 7, pp. 2983-2990, dated 2006.
Jose-Fernando Rosa dos Santos, Soft contact lenses functionalized with pendant cyclodextrins for controlled drug delivery, Biomaterials, vol. 30, pp. 1348-1355, dated 2009.
Tian, Amphiphilic Hyperbranched Polymers Containing Two Types of Beta-Cyclodextrin Segments: Synthesis and Properties, Macromolecular Chemistry and Physics, vol. 210, pp. 2107-2117, dated 2009.
Maciollek, New Generation of Polymeric Drugs: Copolymer from NIPAAM and Cyclodextrin Methacrylate Containing Supramolecular-Attached Antitumor Derivative, Macromolecular Chemistry and Physics, vol. 211, pp. 245-249, dated 2010.
Ren, Noncovalently Connected Micelles Based on a Beta-Cyclodextrin-Containing Polymer and Adamantane End-Capped Poly(E-caprolactone) via Host-Guest Interactions, Journal of Polymer Science: Part A: Polymer Chemistry, vol. 47, pp. 4267-4278, dated 2009.
Chulkova, 18-Crown-6 as a linker for (imino ester)2Pt centers providing their assembly into 1D arrays via hydrogen bonding, Inorganic Chemistry Communications, vol. 13, pp. 580-583, dated 2010.
Garcia et al, Synthesis and radical polymerization of methacrylic monomers with crown ethers in the ester residue: 1,4,7,10-tetraoxacyclododecan-2-ylmethyl methacrylate, Polymer, vol. 45, pp. 1467-1475, dated 2004.
Mahmud, Novel Self-Associating Poly(ethylene oxide)-block-poly(e-caprolactone) Block Copolymers with Functional side Groups on the Polyester Block for Drug Delivery, Macromolecules, vol. 39, pp. 9419-9428, dated 2006.
Perez et al., Poly(lactic acid)-poly(ethylene glycol) nanoparticles as new carriers for the delivery of plasmid DNA, J Controlled Release, vol. 75, pp. 211-224, dated 2001.
P. Couvreur, Nanocapsule Technology: A Review, Drug Carrier Syst. , vol. 19(2), pp. 1-57, dated 2002.
Vauthier et al., Methods for the Preparation and Manufacture of Polymeric Nanoparticles, Expert Review, Pharmaceutical Research, vol. 26, No. 5, pp. 1025-1058, dated 2009.
Lei, Therapeutic angiogenesis, Devising new strategies based on past experiences, Basic Research in Cardiology, vol. 99, pp. 121-132, dated 2004.
Slevin et al., Hyaluronan-mediated angiogenesis in vascular disease: Uncovering RHAMM and CD44 receptor signaling pathways, Matrix Biology, vol. 26, pp. 58-68, dated 2007.
Tessmar et al., Matrices and scaffolds for protein delivery in tissue engineering, Advanced Drug Delivery Reviews, vol. 59, pp. 274-291, dated 2007.
Hern et al., Incorporation of adhesion peptides into nonadhesive hydrogels useful for tissue resurfacing, J. Biomed. Mater. Res., pp. 266-276, dated 1998.
Rezania et al., Biomimetic Peptide Surfaces That Regulate Adhesion, Spreading, Cytoskeletal Organization, and Mineralization of the Matrix Deposited By Osteoblast-like Cells, Biotechnol. Prog., vol. 15, pp. 19-32, dated 1999.
Undin et al., Synthesis of Amorphous Aliphatic Polyester-Ether Homo- and Copolymers by Radical Polymerization of Ketene Acetals, Journal of Polymer Science: J. Poly. Sci. Part A: Polymer Chemistry, vol. 48, pp. 4965-4976, dated 2010.
Lin, Hemocompatibility and cytocompatibility of styrenesulfonate-grafted PDMS-polyurethane-HEMA hydrogel, Colloids and Surfaces B: Biointerfaces, vol. 70, pp. 132-141, dated 2009.
Stella, Prodrugs: the control of drug delivery via bioreversible chemical modification, Drug Delivery Systems, pp. 112-176, dated 1985.
Maeda et al. Targeting and Recanalization after Embolization with Calibrated Resorbable Microspheres versus Hand-cut Gelatin Sponge Particles in a Porcine Kidney Model, J. Vasc. Interv Radiol, vol. 24. pp. 1391-1398, dated 2013.

IMPLANTABLE SWELLABLE BIO-RESORBABLE POLYMER

FIELD OF THE INVENTION

The present invention relates to swellable and bio-resorbable cross-linked polymers liable to be implanted in an individual and optionally to deliver drugs to the individual.

TECHNICAL BACKGROUND

There are schematically three types of resorbable biomaterials. The first one is a biomaterial which occupies a void or a virtual space and is applied for the occlusion of vessels or other cavities (natural or surgical ones), defects such as wrinkles. The second type is a biomaterial which has a pure function as a drug delivery system examples: local delivery in organs such as brain (antimitotic agent), eye (antiangiogenic agent), or cavities (antibiotic or anti-inflammatory agent in surgical voids). The third type is a biomaterial which combines the function of a space filler with a delivery function (embolization microsphere delivering an antimitotic agent, dermal filler containing an anesthesic or anti-inflammatory drug).

The two functions which are required for resorbable drug delivering biomaterials are not fully assumed by the existing resorbable biomaterials. Although they have individually some interesting properties, they don't possess enough of these properties to be proposed as a multifunction implantable biomaterial. An ideal material should swell in a controlled way in situ after implantation, deliver a drug in controlled manner in terms of time and rate and finally resorb after its delivery. The following examples, drawn from the field of embolization and tissue bulking, are given to illustrate the insufficiencies of the existing resorbable materials.

In the field of embolization, several products have individually one interesting property. Gelatin sponges are biodegradable after implantation in tissues or injection in cavities, ducts or vessels. They can easily be impregnated with physiological saline and/or contrast media. However, after their hydration they loose their shape and resistance. In addition, there is a great variability in resorption speed, which is influenced by many factors such as nature, homogeneity, size, enzymatic potential, and local inflammatory response. Moreover, since the mass of resorbable gelatin may vary in large proportions, the resorption time of the plug will consequently also take a variable time.

Dextran starch microspheres (Spherex® from Pharmacia; Embocept® from Pharmacept) are non-toxic, readily degradable and notably used to provide temporary vascular occlusion, mainly for the treatment of tumor when co-administered with chemotherapeutic drugs. However, they suffer from several limitations. First of all, these microspheres are available only in small sizes, with diameters below 100 μm. Such a small diameter does not allow targeted embolization, particularly for proximal occlusion. Besides, resorption is fast, with a usual half life below 1 hour, and cannot be accurately predicted since depends on the enzymatic capability to resorb a given microspheres volume.

Water-absorbent dry microspheres based on acrylic and PVA copolymers have also been proposed as swellable implants for embolization (Osuga et al. (2002) *J Vasc Interv Radiol*. 13:929-34). In a commercial presentation (Quadrasphere®, Biosphere Medical), these microspheres are under a dry form. For their use they are mixed with physiological saline, and/or iodinated contrast media. Compared to their initial size, their final size after water uptake varies according to the ionic charge of the medium (×2 or ×4 in saline and contrast medium respectively). However the final size varies too much to allow for their controlled final volume after implantation, which is a serious limitation for their use. Besides, these microspheres are not resorbable.

In the field of soft tissue repair and augmentation, a number of products have been used. However, they present all some disadvantages:

Silicone gel (or silicone oil) is easy to use. However, the migration of droplets of silicone into the tissues situated below the point of injection, by simple gravity, has been observed after injection. It appears also that liquid silicone tends to migrate to distant body part causing a variety of physiological and clinical problems. Indeed, silicone is frequently the cause of chronic inflammation, of formation of granulomas, and even of tardive allergic reactions. Silicone is not biodegradable, and it is often found in the liver. Therefore, the FDA has prohibited the use of liquid silicone in humans.

Collagen suspensions have been very widely used in the last ten years. The results have however been quite disappointing since collagen is resorbed within 1 to 3 months. It should also be noted that collagen is of bovine origin and allergic reactions to the bovine proteins are noted in about 2% of patients. In an attempt to solve these problems, crosslinked collagen was introduced to extend effective treatment times to approximately six months. However allergic reactions still occur.

Hyaluronate gels provided a good alternative by virtue of their biocompatibility and their lack of toxicity. They are moreover widely used in eye surgery. However, their rapid bioresorbability (maximum 2 months) makes them ineffective for use in plastic surgery. Furthermore, hyaluronic gels can be source of acute or delayed hypersensitivity and can generate severe local inflammatory response.

Particles which are either biodegradable (PLGA) or not (acrylamide, PMMA, EMA) can also be used.

Non biodegradable particles such as poly(methyl methacrylate) (PMMA) microspheres are permanent. Because of that, the body can mount a foreign body response to these polymers and forms a tight fibrous capsule around the material. Furthermore there is a risk of migration of this material away from the injection site.

The disadvantages of biodegradable particles such as PLGA are their tendency to aggregate prior to and/or during clinical application which will render difficult their injection and/or form hard, insoluble nodules at the injection site, causing oedema and swelling and, most of the times, requiring corrective medical intervention. Furthermore they undergo a prolonged inflammatory response as long as the degradation takes place and subunits are released.

It is also known to use a combination of gel material (hyaluronate gel and/or collagen gel) containing microparticles (degradable or not). In particular known commercial products are New-Fill Sculptra® from Sanofi Aventis (poly-L-lactic acid microparticles suspended in sodium carboxymethylcellulose, mannitol and water) and Artefill®, Artecoll® from Artes medical (poly(methyl methacrylate) microspheres suspended in collagen gel). However, the combination of gel and microparticles do not solve the above mentioned problems. The carrier gel disappears from the site within 1 to 3 months and at the same time the host response to the remaining microparticles gradually makes up for the loss of filling effect in a more permanent manner. The host foreign-body response runs its course and ends up until a permanent de novo fibrous scar tissue is embedding the intended filler agent of these gels.

Furthermore, literature has since many years established, for solid implants, that tissue ingrowths in the implanted biomaterial depend in a large part on the porosity of the material. Scaffolds and/or matrix with controlled porosity are required to allow cell ingrowth, nutrient diffusion and sufficient formation of vascular networks. Mean pore size is an essential aspect of scaffolds for tissue-engineering. If pores are too small cells cannot migrate in towards the center of the construct limiting the diffusion of nutrients and removal of waste products. Conversely, if pores are too large there is a decrease in specific surface area available limiting cell attachment. The permeability of scaffolds and other three-dimensional constructs used for tissue engineering applications is important as it controls the diffusion of nutrients in and waste out of the scaffold as well as influencing the pressure fields within the construct (O'Brien Technol Health Care. 2007; 15(1):3-17).

To facilitate the injection of the particles in needles having small diameter, several dermal fillers contain a natural polymer gel, which is resorbed quickly after the implantation. Their resorbtion time is usually homogeneous and occurs generally quickly. Since these gels represent the major part of the injected volume (80% in some cases), it leads the gels to lose a large part of their filler effect from disappearance. This component is said to favor the tissue ingrowth. However since they contain few matters and have a high water content (about 90%) these gels offer to the body a structure, which is often too loose to constitute a matrix for tissue ingrowth. Therefore, most combination gels (gel and particles) are not actually efficient to facilitate the tissue ingrowth between the particles or between the polymer threads.

Microspheres have been proposed to prepare solid scaffolds for tissue engineering by Brown (Brown J Biomed Mater Res B Appl Biomater. 2008 August; 86B(2):396-406). He has applied a technique of solvent/non-solvent sintering which creates porous polymeric microsphere scaffolds suitable for tissue engineering purposes with control over the resulting porosity, average pore diameter, and mechanical properties. Five different biodegradable biocompatible polyphosphazenes exhibiting glass transition temperatures from −8 to 41° C. and poly (lactide-co-glycolide), (PLGA) a degradable polymer used in a number of biomedical settings, were examined to study the versatility of the process and benchmark the process to heat sintering. Parameters such as: solvent/non-solvent sintering, solution composition and submersion time affect the sintering process. PLGA microsphere scaffolds fabricated with solvent/non-solvent sintering exhibited an interconnected porosity and pore size of 31.9% and 179.1 micrometers, respectively which was analogous to that of conventional heat sintered PLGA microsphere scaffolds. Biodegradable polyphosphazene microsphere scaffolds exhibited a maximum interconnected porosity of 37.6% and a maximum compressive modulus of 94.3 MPa. Solvent/non-solvent sintering is an effective strategy for sintering polymeric microspheres, with a broad spectrum of glass transition temperatures, under ambient conditions making it an excellent fabrication route for developing tissue engineering scaffolds and drug delivery vehicles.

The patent WO 2009049230 describes a solid scaffold including a plurality of biocompatible microspheres sets linked together by a partial melding of the microspheres in a solvent or solvent system gaseous sub-critical $CO_2$ to form a three-dimensional matrix. The matrix's pores, defined by and disposed between the microspheres, range from about 200 micrometers to about 1650 micrometers. The different sets of microspheres can have different characteristics, such as polymer nature, particle size, particle size distribution, type of bioactive agent, type of bioactive agent combination, bioactive agent concentration, amount of bioactive agent, rate of bioactive agent release, mechanical strength, flexibility, rigidity, color, radiotranslucency, radiopaqueness. A type of microspheres can be made from a biodegradable polymer such as poly-lactide-co-glycolide or poly(lactic-co-glycolic acid).

However the diameter of the porous spaces located between the microspheres in a sediment of microsphere having a compacity of 60% is rather small, about 13% of the microspheres diameter. It means that in a cluster of microspheres having a mean diameter of 100 μm, the size of the inter-microsphere pore is about 13 μm. If one consider that the clusters resulting from an injection of a microspheres suspension have a lower compacity than 60%, one could consider that in such clusters the pore diameter ranges from 13 μm to a few dozens of micrometers. Such an inter-microsphere pore size is not favourable to tissue ingrowth in the clusters. The minimum pore diameter for one cell like a macrophage is about 15 μm. Moreover some cells like preadipocytes enlarge during differentiation due to incorporation of lipids and then need large pores sizing at least 40 μm (Von Heimburg, Biomaterials. 2001 March; 22(5):429-38).

The growth of an organised tissue in a scaffold needs both large pore size and large void fraction. Void Fraction (VF) of microspheres sediments, which ranges from 60% to 70% is insufficient to allow an efficient filling up by a functional tissue. Zeltinger had demonstrated that Void Fraction, independently from pore size, was a major determinant of scaffold colonisation. Scaffold with 75% VF were unsuitable for tissue formation while those with 90% VF were suitable for tissue formation when pore size was over 38 μm (Zeltinger Tissue Eng. 2001 October; 7(5):557-72). In summary the natural microspheres sediments/beds obtained by microspheres injections in tissues are very far from offering to tissue ingrowth a convenient pore size and a sufficient void fraction.

Therefore there is a need to find a new product for soft tissue repair and augmentation useful as scaffolds and/or matrix for tissue ingrowth.

It has been proposed in patent No PCT/EP 2010/063227 to synthesize swellable and bio-resorbable cross-linked polymers liable to be implanted. However after degradation of these polymers the residues presents in the body may have a too high molecular weight. Therefore, they tend to accumulate in the kidney of the patient which could be detrimental for its health.

Furthermore, when the polymer is loaded with drugs it is important to be able to control over time the rate of release of said drug. The controlled release of the drug is achieved by diffusion, swelling of the network or degradation of the polymeric matrix. Drug loading can be done by chemical conjugation or physical entrapment, and so the respective drug release processes are dependent on the type of encapsulation.

In the chemically conjugated drug, the loading is predictable since it is directly connected to the chemistry of the particles. The release should occur by hydrolysis of the linker between the polymer network and the drug. To control the release, one could play on the chemical composition of the linker. However, it has been observed that for hydrophobic drugs, the degradation of the polymer network could be slow down. Indeed, apolar structure of the drug may decrease the swelling of polymer and so less water molecules will be in contact with the hydrolysable groups of the polymer. Moreover, for the same reason, hydrophobic structure inside the polymer will considerably reduce the release.

For the physically entrapped drug, the loading could be done either by passive adsorption (swelling of the polymer into a drug solution) or by ionic interaction. Efficiency of encapsulation depends mainly on the compatibility between both structures and/or favourable interactions. Generally, polymer prepared using the PLGA system exhibits release kinetics based on both erosion and diffusion. In this type of system, an initial burst or rapid release of drug is observed. This burst effect can result in unwanted side effects in patients to whom the polymers have been administered. To obtain a controlled and/or sustained release of the drugs with crosslinked microspheres of polymer, two main factors may affect drug release: nature and extent of cross-linking. For low molecular weight drugs (typically below 1000 Da), it is not easy to play with these two factors since decreasing the mesh size of the polymer network, will not or poorly modify the diffusion of molecules through the meshes before degradation of the polymer. Like the covalently conjugate system, entrapment of hydrophobic drugs reduces the swelling of the polymer and may change the degradation rate of the resorbable system.

It is therefore a goal of the present invention to solve the above mentioned problems.

SUMMARY OF THE INVENTION

The present invention arises from the unexpected finding, by the inventors, that the presence of a cyclic monomer having an exo-methylene group during the polymerization of the polymer described in patent No PCT/EP 2010/063227, can lower the molecular weight of the residue obtained after degradation of the polymer without modifying the mechanical properties of the polymer.

The use of this kind of monomer during the polymerization will increase the number of labile points into the main chain of the polymer network and therefore lower the molecular weight of the residue obtained after hydrolytic degradation. This feature will therefore avoid the unwanted accumulation of polymers in kidneys.

Furthermore the use of this monomer for preparing the polymer previously described in patent No PCT/EP 2010/063227 will not modify the ability of the polymer to load drugs while keeping a good efficiency and preserving the sustained release of a low molecular weight drug, whatever the method used for the loading of drug. Indeed, introduction of the drug whatever the method used will not modify the polymer properties. So, the present invention relies on the conjugation of both aspects ie loading efficiency/sustained release coupled with the conservation of the initial properties of the polymer:

In addition, where the polymer is provided as a spherical particle, sphericity can be maintained even upon swelling.

Besides, it was also evidenced by the Applicant that in animal experiments performed in sheep shoulder joints, unlike microspheres of the prior art, polymer of the invention-based microspheres were quickly incorporated into the synovial tissue and that their residency time in synovium was at least of several weeks (1 month), making the microspheres of the invention suitable for delivering drug in the synovium for several weeks or months.

Furthermore it has been found surprisingly that the polymer described in PCT/EP 2010/063227 which is obtained by the polymerization described in this document in which the cyclic monomer having an exo-methylene group is not used are useful for soft tissue repair and augmentation since resorption of microspheres obtained using this kind of polymer does not induce any inflammatory response. It has also been found that this type of polymer is also suitable as a matrix for tissue ingrowth. Indeed it is easy to prepare microsphere of this polymer having different diameter and resorption time and combining them in a single composition for injection.

However, in order to avoid accumulation in the kidney of the residue obtained after resorption of the polymer it is preferable to use a polymer obtained by polymerization in which cyclic monomer having an exo-methylene group is used.

The present invention thus relates to a polymer obtainable from the polymerization of:
(i) at least one monomer of formula (I)

$$(CH_2=CR_1)CO-K \qquad (I)$$

wherein:
K represents O—Z or NH—Z, Z representing $(CR_2R_3)_m$—$CH_3$, $(CH_2-CH_2-O)_m$—H, $(CH_2-CH_2-O)_m$—$CH_3$, $(CH_2)_m$—$NR_4R_5$ with m representing an integer from 1 to 30;
$R_1, R_2, R_3, R_4$ and $R_5$ independently represent H or a $C_1$-$C_6$ alkyl;
ii) at least between 0.1 and 50% mol, advantageously between 1 and 30% mol, more advantageously between 1 and 20 mol %, typically between 1 and 10 mol %, of a cyclic monomer having an exo-methylene group of formula (II):

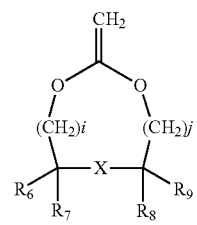

wherein:
R6, R7, R8 and R9 represent independently H or a $C_5$-$C_7$ aryl group or R6 and R9 are absent and R7 and R8 form together with the carbon atom on which they are bonded a $C_5$-$C_7$ aryl group;
i and j represent independently an integer chosen between 0 and 2, advantageously i and j are chosen between 0 and 1, more advantageously i=j, still more advantageously, i=j=1;
X represents either O or X is not present and in this latter case, CR6R7 and CR8R9 are linked via a single bond C—C
and
(iii) at least one bio-resorbable block copolymer cross-linker.

In a specific embodiment of the invention, the above-defined polymer is obtainable from the polymerization of:
(i) at least one monomer of formula (I)

$$(CH_2=CR_1)CO-K \qquad (I)$$

wherein:
K represents O—Z or NH—Z, Z representing $(CR_2R_3)_m$—$CH_3$, $(CH_2-CH_2-O)_m$—H, $(CH_2-CH_2-O)_m$—$CH_3$, $(CH_2)_m$—$NR_4R_5$ with m representing an integer from 1 to 30;
$R_1, R_2, R_3, R_4$ and $R_5$ independently represent H or a $C_1$-$C_6$ alkyl;
ii) at least between 1 and 20 mol %, advantageously between 1 and 10 mol %, of a cyclic monomer having an exo-methylene group of formula (II):

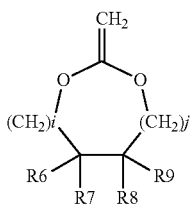

(II)

wherein:
R6, R7, R8 and R9 represent independently H or a $C_5$-$C_7$ aryl group or R6 and R9 are absent and R7 and R8 form together with the carbon atom on which they are bonded a $C_5$-$C_7$ aryl group;

i and j represent independently an integer chosen between 0 and 2, advantageously i and j are chosen between 0 and 1, more advantageously i=j, still more advantageously, i=j=1 and (iii) at least one bio-resorbable block copolymer cross-linker.

In another specific embodiment of the invention, the above-defined polymer is obtainable from the polymerization of the at least one monomer (I), at least between 0.1 and 50% mol, advantageously between 1 and 30% mol, more advantageously between 1 and 20 mol %, typically between 1 and 10 mol %, of 2-Methylene-1,3,6-Trioxocane (MTC) of the following formula (II):

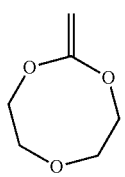

and the at least one bio-resorbable block copolymer cross-linker (iii).

Advantageously according to the invention, the above-defined polymer is obtainable from the polymerization of the at least one monomer, the at least one cyclic monomer, the at least one bio-resorbable block copolymer cross-linker, and (iv) further at least one chain transfer agent.

Oftentimes, the active species used to initiate polymerization are highly reactive and may conduct in some cases to undesirable side reactions such as chain transfer. This can lead to the production of short or long branches or even more problematically to the formation of non resorbable crosslinking (Scorah 2006, Polym. Bull. 57, 157-167). These structural changes can have adverse effects on the biocompatibility of the material. To avoid these side reactions, some chain transfer agents may be added, advantageously in appropriate levels, to the monomer solution without affecting the network formation. These molecules with high transfer reactivity, also called "regulators", are very efficient even at small concentrations. Furthermore the use of at least one transfer agent is an additional way to reduce/control the molecular weight of the polymer chain residue (Loubat 2001, Polym. Int. 50, 375-380; Odian, G. "Principles of polymerization" 3$^{rd}$ ed., J. Wiley, New York 1991).

Advantageously, the at least one chain transfer agent is selected from the group consisting of monofunctional or polyfunctional thiols, alkyl halides, transition metal salts or complexes and other compounds known to be active in free radical chain transfer processes such as 2,4-diphenyl-4-methyl-1-pentene.

Particularly advantageously, the at least one chain transfer agent is a cycloaliphatic, or preferably aliphatic, thiol typically having from 2 to about 24 carbon atoms, and having or not a further functional group selected from the groups amino, hydroxy and carboxy.

Examples of particularly preferred chain transfer agents are thioglycolic acid, 2-mercaptoethanol, dodecane thiol and hexane thiol.

According to the invention, the at least one chain transfer agent may be present in the reaction mixture in an amount of, for example, from 0.1 to 10%, preferably from 1 to 4%, and in particular from 1.5 to 3.5% by mole, relative to the number of moles of monofunctional monomers.

In an embodiment of the invention, the above-defined polymer is obtainable from the polymerization of the at least one monomer, the at least one cyclic monomer, the at least one bio-resorbable block copolymer cross-linker, optionally at least one chain transfer agent as defined above and at least one further monomer selected from the list comprising:

(i) a drug-carrying monomer of the following formula (IV):

$$(CH_2\!\!=\!\!CR_{13})CO\text{-}L_1\text{-}D \qquad (IV)$$

wherein:
$R_{13}$ represents H or a $C_1$-$C_6$ alkyl;
$L_1$ represents a linker moiety having from 1 to 20 carbon atoms comprising a hydrolyzable function linked to the D group;
the D group represents a drug or a prodrug; and (ii) a charged, ionisable, hydrophilic, or hydrophobic monomer of the following formula (V):

$$(CH_2\!\!=\!\!CR_{14})CO\text{-}M\text{-}E \qquad (V)$$

wherein:
$R_{14}$ represents H or a $C_1$-$C_6$ alkyl;
M represents a single bond or a linker moiety having from 1 to 20 carbon atoms;
E represents a charged, ionisable, hydrophilic, or hydrophobic group having 100 atoms at the most.

In another embodiment of the invention, the above-defined polymer is obtainable from the polymerization of the at least one monomer, the at least one cyclic monomer, the at least one bio-resorbable block copolymer cross-linker, and the drug-carrying monomer.

In yet another embodiment of the invention, the above-defined polymer is obtainable from the polymerization of the at least one monomer, the at least one bio-resorbable block copolymer cross-linker, the at least one cyclic monomer and the at least one charged, ionisable, hydrophilic, or hydrophobic monomer.

These embodiments are advantageous in that where the polymer of the invention is polymerized from a drug-carrying monomer as defined above, the polymer can be used as a drug delivery system. Besides, where the polymer of the invention is polymerized from a charged, ionisable, hydrophilic, or hydrophobic monomer as defined above, the polymer may present with various physico-chemical surface characteristics enabling loading, i.e. non-covalently adsorbing, drugs to be delivered.

Thus, in a further embodiment of the invention, the above defined polymer is loaded with a drug or a prodrug or a diagnostic agent.

In another embodiment of the invention, the above-defined polymer is obtainable from the polymerization of the at least one monomer, the at least one cyclic monomer, the at least one block copolymer cross-linker, the at least one drug-carrying monomer, optionally the at least one charged, ionisable, hydrophilic, or hydrophobic monomer, and at least one hydrophilic monomer of the following formula (IX):

$$(CH_2=CR_{23})CO-Q \quad (IX)$$

wherein:
R$_{23}$ represents H or a C$_1$-C$_6$ alkyl;
Q represents a C$_1$-C$_{100}$ alkyl optionally substituted by at least one substituent selected from the group consisting of a hydroxyl, an oxo or an amino function.

The incorporation into the polymer of the invention of the above-defined hydrophilic monomer is advantageous in that it allows modulating the release of the drug by the polymer of the invention.

The present invention also relates to at least one polymer as defined above for use as a medicinal product advantageously intended for the correction of skin ageing and/or for wound healing and/or for tissular reconstruction and/or for soft tissue repair, and/or for the treatment of inflammation, cancer, arteriovenous malformations, cerebral aneurysm, gastrointestinal bleeding, epistaxis, primary post-partum haemorrhage and/or surgical haemorrhage and/or for regenerating tissue in human or animals.

The present invention also relates to a pharmaceutical composition comprising at least one polymer as defined above, in association with a pharmaceutically acceptable carrier, advantageously intended for administration by injection.

In particular it relates to an injectable pharmaceutical composition comprising
(a) a polymer according to the present invention having a spherical shape of a diameter of between 50 and 500 µm and a resorption time of between a few days to 3 weeks;
(b) a polymer according to the present invention having a spherical shape of a diameter of between 50 and 500 µm and a resorption time of between one to 3 months;
and
(c) at least one pharmaceutically acceptable excipient.

Advantageously, in the composition according to the present invention, the spherical particles of polymer (a) and (b) do not have the same diameter, advantageously the diameter of the spherical particles of polymer (a) is of between 100 and 300 µm and the diameter of the spherical particles of polymer (b) is of between 300 and 500 µm.

The present invention also relates to an implant containing at least one polymer as defined above or the composition as defined above.

DETAILED DESCRIPTION OF THE INVENTION

Bio-Resorbable Block Copolymer

As intended herein, the expression "bio-resorbable" means that the block copolymer is degraded or cleaved when administered into a living organism, preferably a mammal, in particular a human, organism. As intended herein "bio-resorbable" indicates that the block copolymer may be hydrolyzed.

As intended therein, the expression "copolymer cross-linker" is intended to mean that the copolymer contains a functional group at at least two of its extremities in order to link together several polymer chains. Advantageously this functional group contains a double bond.

Preferably, the bio-resorbable block copolymer cross-linker as defined above is linear and advantageously it presents (CH$_2$=(CR$_{10}$))— groups at both its extremities, wherein R$_{10}$ independently represents H or a C$_1$-C$_6$ alkyl. Preferably also, the bio-resorbable block copolymer cross-linker is a diblock or a triblock copolymer. Block copolymer crosslinker are more advantageous than statistic copolymer since, in particular if one of the block contains PEG, they have the tendency to attract more water molecules and therefore to be more easily hydrolysable. Furthermore, it is easy to change the size of the block and hence to adapt the rate of biodegradability of the polymer according to the present invention in function of its intended use.

It is also preferred that the block of the bio-resorbable block copolymer cross-linker as defined above is selected from the groups consisting of polyethylene glycol (PEG), poly-lactic acid (also named poly-lactide) (PLA), poly-glycolic acid (also named poly-glycolide) (PGA), poly-lactic-glycolic acid (PLGA) and poly(caprolactone) (PCL).

As is well known to one of skill in the art, PEG, PLA, PGA and PCL may be represented as follows, n representing their degree of polymerization:

-PEG:

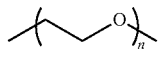

-PLA:

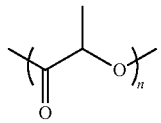

-PGA:

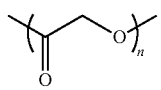

-PCL

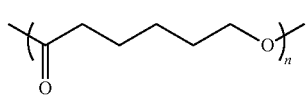

For PLGA which comprises both lactide and glycolide units, the degree of polymerizaton is the sum of the number of lactide and glycolide units.

More preferably, the bio-resorbable block copolymer cross-linker as defined above is of the following formula (III):

$$(CH_2=CR_{11})CO-(X_n)_l-PEG_p-Y_k-CO-(CR_8=CH_{12}) \quad (II)$$

wherein:
R$_{11}$ and R$_{12}$ independently represent H or a C$_1$-C$_6$ alkyl;
X and Y independently represent PLA, PGA, PLGA or PCL;
n, p, and k respectively represent the degree of polymerization of X, PEG, and Y, n and k independently being integers from 1 to 150, and p being an integer from 1 to 100;
l represents 0 or 1.

Most preferably, the bio-resorbable block copolymer cross-linker as defined above is of a formula selected from the group consisting of:

$$(CH_2=CR_{11})CO\text{-}PLA_n\text{-}PEG_p\text{-}PLA_k\text{-}CO-(CR_{12}=CH_2),$$

$$(CH_2=CR_{11})CO\text{-}PGA_n\text{-}PEG_p\text{-}PGA_k\text{-}CO-(CR_{12}=CH_2),$$

$$(CH_2=CR_{11})CO\text{-}PLGA_n\text{-}PEG_p\text{-}PLGA_k\text{-}CO-(CR_{12}=CH_2),$$

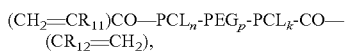

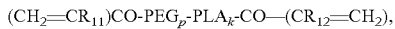

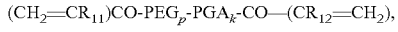

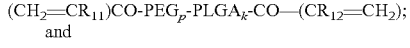

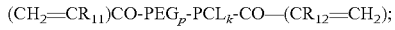

wherein $R_{11}$, $R_{12}$, n, p and k are as defined above.

Polymer

As will be clear to one of skill in the art the polymer of the invention is a bio-resorbable (i.e. hydrolizable) cross-linked polymer. In particular the polymer of the invention is constituted of at least one chain of polymerized monomers as defined above which contains between 0.1 and 50% mol, advantageously between 1 and 30% mol, more advantageously between 1 and 20% mol, typically between 1 and 10% mol of ester linkage coming from the cyclic monomer having an exo-methylene group, which at least one chain is cross-linked by bio-resorbable block copolymer cross-linkers as defined above.

Advantageously, the polymer of the invention is swellable, i.e. has the capacity to absorb liquids, in particular water. Therefore this type of polymer is called hydrogel.

As will also be clear to one of skill in the art, and by way of example, the monomers of the invention may also be represented as follows:

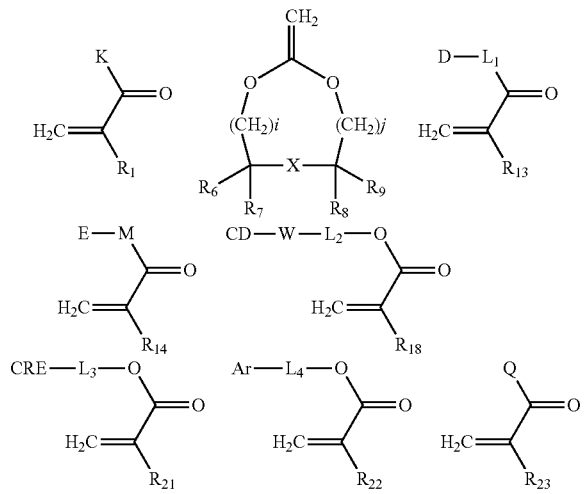

Upon polymerization the monomers of the invention may then be represented as follows:

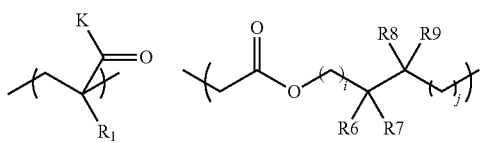

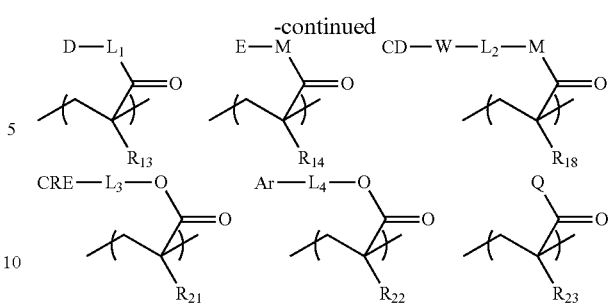

Preferably, the monomer of formula (I) as defined above is selected from the group consisting of sec-butyl acrylate, n-butyl acrylate, t-butyl acrylate, t-butyl methacrylate, methylmethacrylate, N-dimethyl-aminoethyl(methyl)acrylate, N,N-dimethylaminopropyl-(meth)acrylate, t-butylaminoethyl(methyl)acrylate, N,N-diethylaminoacrylate, acrylate terminated poly(ethylene oxide), methacrylate terminated poly(ethylene oxide), methoxy poly(ethylene oxide) methacrylate, butoxy poly(ethylene oxide) methacrylate, acrylate terminated poly(ethylene glycol), methacrylate terminated poly(ethylene glycol), methoxy poly(ethylene glycol) methacrylate, butoxy poly(ethylene glycol) methacrylate.

Most preferably, the monomer of formula (I) as defined above is poly(ethylene glycol) methyl ether methacrylate.

Preferably, the cyclic monomer of formula (II) is selected from the group consisting of 2-methylene-1,3-dioxolane, 2-methylene-1,3-dioxane, 2-methylene-1,3-dioxepane, 2-Methylene-1,3,6-Trioxocane and derivatives thereof, in particular benzo derivatives and phenyl substituted derivatives, advantageously from the group consisting of 2-methylene-1,3-dioxolane, 2-methylene-1,3-dioxane, 2-methylene-1,3-dioxepane, 2-methylene-4-phenyl-1,3-dioxolane, 2-Methylene-1,3,6-Trioxocane and 5,6-benzo-2-methylene-1,3dioxepane, more advantageously from the group consisting of 2-methylene-1,3-dioxepane, 5,6-benzo-2-methylene-1,3dioxepane and 2-Methylene-1,3,6-Trioxocane.

Besides, it is preferred that E is selected from the group constituted of COOH, COO$^-$, SO$_3$H, SO$_3^-$, PO$_4$H$_2$, PO$_4$H$^-$, PO$_4^{2-}$, NR$_{15}$R$_{16}$, NR$_{15}$R$_{16}$R$_{17}^+$, in which $R_{15}$, $R_{16}$ and $R_{17}$ independently represent H or a $C_1$-$C_6$ alkyl, a $C_1$-$C_{20}$ alkyl group, a $C_5$-$C_{20}$aryl group, a (5-30-members)heteroaryl group containing an heteroatom chosen in the group consisting of O, N or S, a O—$C_5$-$C_{20}$aryl group and a O-(5-30-members)heteroaryl group, a crown ether, and a cyclodextrin.

Preferably, the charged, ionisable, hydrophilic, or hydrophobic monomer is a cationic monomer, advantageously selected from the group consisting of -(methacryloyloxy) ethyl phosphorylcholine, 2-(dimethylamino)ethyl(meth) acrylate, 2-(diethylamino)ethyl(meth)acrylate and 2-((meth) acryloyloxy)ethyl]trimethylammonium chloride, more advantageously the cationic monomer is diethylamino)ethyl (meth)acrylate. Advantageously the polymer according to the present invention is obtained by using between 1 and 30 mol % of the above-mentioned cationic monomer based on the total amount of the monomer, more advantageously between 10 and 15 mol %.

In another advantageous embodiment, the charged, ionisable, hydrophilic, or hydrophobic monomer is an anionic monomer advantageously selected from the group consisting of acrylic acid, methacrylic acid, 2-carboxyethyl acrylate, 2-carboxyethyl acrylate oligomers, 3-sulfopropyl(meth) acrylate potassium salt and 2-(methacryloyloxy)ethyl]dimethyl-(3-sulfopropyl)ammonium hydroxide. Advantageously the polymer according to the present invention is obtained by using between 1 and 30 mol % of the above-mentioned anionic monomer based on the total amount of the monomer, more advantageously between 10 and 15 mol %.

In an advantageous embodiment, E is a cyclodextrin and the charged, ionisable, hydrophilic, or hydrophobic monomer has the following formula (VI):

$(CH_2=CR_{18})COO-L_2-W-CD$ (VI)

wherein:
- $R_{18}$ represents H or a $C_1$-$C_6$ alkyl;
- $L_2$ represents a linker moiety having from 1 to 20 carbon atoms optionally substituted by a hydroxyl group;
- W represents a —NH—, —CO—, —NH—$R_{19}$—NH—, —CO—$R_{19}$—CO— or -triazolyl-$R_{20}$— group in which $R_{19}$ and $R_{20}$ represent independently of each other a $C_1$-$C_6$ alkyl group;
- CD represents a cyclodextrin.

Advantageously the polymer according to the present invention is obtained by using between 1 and 40 mol %, typically between 1 and 20 mol %, of the above-mentioned monomer of formula (VI) based on the total amount of the monomer.

In the present invention, the cyclodextrin, can be any known cyclodextrin, in particular selected in the group consisted of beta-cyclodextrin, methyl-beta-cyclodextrin, gamma-cyclodextrin or hydroxypropyl-gamma-cyclodextrin. Advantageously, it is beta-cyclodextrin.

Examples of (meth)acrylic structures bearing cyclodextrin residue are proposed in the following references: Macromol Chem Phys 2009, 210, 2107; Macromol Chem Phys 2010, 211, 245; J polym Sci 2009, 47, 4267.

In another advantageous embodiment, E is a crown ether and the charged, ionisable, hydrophilic, or hydrophobic monomer has the following formula (VII):

$(CH_2=CR_{21})COO-L_3-CRE$ (VII)

wherein:
- $R_{21}$ represents H or a $C_1$-$C_6$ alkyl;
- $L_3$ represents a linker moiety having from 1 to 20 carbon atoms optionally substituted by a hydroxyl group, advantageously chosen in the group consisting of $C_1$-$C_6$ alkyl and $C_1$-$C_6$ alkyl (O$C_1$-$C_6$ alkyl) the alkyl group being optionally substituted by an hydroxyl group;
- CRE represents a crown ether.

Advantageously the polymer according to the present invention is obtained by using between 1 and 50 mol %, typically between 1 and 20 mol % of the above-mentioned monomer of formula (VII) based on the total amount of the monomer.

Examples of (meth)acrylic structures bearing crown ether residue are proposed in the following references: Polymer 2004, 45, 1467; Macromolecules 2003, 36, 1514.

In still another advantageous embodiment, E is selected from the group constituted of a $C_5$-$C_{20}$ aryl group, a (5-30-members) heteroaryl group containing an heteroatom chosen in the group consisting of O, N or S, a O—$C_5$-$C_{20}$aryl group and a O-(5-30-members) heteroaryl group and the charged, ionisable, hydrophilic, or hydrophobic monomer has the following formula (VIII):

$(CH_2=CR_{22})COO-L_4-Ar$ (VIII)

wherein:
- $R_{22}$ represents H or a $C_1$-$C_6$ alkyl;
- $L_4$ represents a linker moiety having from 1 to 20 carbon atoms optionally substituted by a hydroxyl group, advantageously chosen in the group consisting of $C_1$-$C_6$ alkyl and $C_1$-$C_6$ alkyl (O$C_1$-$C_6$ alkyl), the alkyl group being optionally substituted by an hydroxyl group;
- Ar represents a $C_5$-$C_{20}$ aryl, (5-30-members) heteroaryl containing an heteroatom chosen in the group consisting of O, N or S, O—$C_5$-$C_{20}$aryl or O-(5-30-members)heteroaryl group containing an heteroatom chosen in the group consisting of O, N or S.

Advantageously the polymer according to the present invention is obtained by using between 1 and 50 mol %, typically between 1 and 30 mol % of the above-mentioned monomer of formula (VIII) based on the total amount of the monomer, more advantageously between 5 and 15 mol %.

Advantageously the charged, ionisable, hydrophilic, or hydrophobic monomer of formula (VIII) as defined above is selected from the group consisting of 2-(4-benzoyl-3-hydroxyphenoxy)ethyl(meth)acrylate, 2-hydroxy-3-phenoxypropyl (meth)acrylate, ethylene glycol phenyl ether(meth)acrylate, benzyl methacrylate, 9H-carbazole-9-ethylmethacrylate.

It is also preferred that the hydrophilic monomer as defined above is selected from the group consisting of (meth)acrylamide, 2-hydroxyethyl(meth)acrylate, N-vinyl-2-pyrrolidone, butyl(meth)acrylate, acrylic acid, acrylic anhydride, N-trishydroxymethyl methacrylamide, glycerol mono(meth)acrylate, hydroxypropyl(meth)acrylate, 4-hydroxybutyl (meth)acrylate.

It is also preferred that $L_1$, $L_2$, $L_3$ and $L_4$ and M are of the following formula:

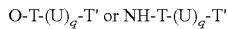

O-T-$(U)_q$-T' or NH-T-$(U)_q$-T' wherein T and T', identical or different, represent a $C_1$-$C_6$ alkyl chain optionally substituted by one or more hydroxyl, oxo, or amino group, U represents an hydrolysable function, such as an ester, amide, a disulfide, an amino-oxy or anhydride function, and q represents an integer from 0 to 2 for M and from 1 to 2 for $L_1$, $L_2$, $L_3$ and $L_4$.

The polymer of the invention can be readily synthesized by numerous methods well-known to one of skill in the art. By way of example, the polymers of the invention can be obtained by suspension polymerization as described below and in the Examples.

A direct suspension may proceed as follows: (a) stirring or agitating a mixture comprising (i) at least one monomer as defined above, at least one cyclic monomer as defined above and at least one bio-resorbable block copolymer cross-linker; (ii) a polymerization initiator present in amounts ranging from 0.1 to approximately 2 parts per weight per 100 parts by weight of the monomers and a radical initiator, such as AIBN; (iii) a surfactant in an amount no greater than about 5 parts by weight per 100 parts by weight of the monomers, preferably no greater than about 3 parts by weight and most preferably in the range of 0.5 to 1.5 parts by weight; and (iv) water to form an oil in water suspension; and (b) polymerizing the monomer(s) and the bio-resorbable block copolymer cross-linker.

An inverse suspension may proceed as follows: (a) stirring or agitating a 30 mixture comprising: (i) at least one monomer as defined above, and at least one bioresorbable block copolymer cross-linker; (ii) a polymerization initiator present in amounts ranging from 0.1 to approximately 2 parts per weight per 100 parts by weight of the monomers; (iii) a surfactant in an amount no greater than about 5 parts by weight per 100 parts by weight of the monomers, preferably no greater than about 3 parts by weight and most preferably in the range of 0.5 to 1.5 parts by weight; and (iv) oil to form a water in oil suspension; and (b) polymerizing the monomers and the bio-resorbable block copolymer cross-linker.

Drug

As intended here the drug or prodrug as defined above can be of any type and intended for the prevention or treatment of any disease or impairment and or for decreasing or suppressing pain. In particular it is a low molecular weight drug or prodrug or small biological agent, advantageously having a molecular weight below 5000 Da, typically below 1000 Da. More advantageously, it is a hydrophobic drug.

In the sense of the present invention the term "prodrugs" is intended to mean any drug derivatives which are degraded in vivo to yield the drug having the therapeutical activity. Prodrugs are usually (but not always) of lower potency at the target receptor than the drugs to which they are degraded. Prodrugs are particularly useful when the desired drug has chemical or physical properties, which make its administration difficult or inefficient. For example, the desired drug may be only poorly soluble, it may be poorly transported across the mucosal epithelium, or it may have an undesirably short plasma half-life. Further discussion of prodrugs may be found in Stella, V. J. et al. "Prodrugs", *Drug Delivery Systems,* 1985, 112-176, Drugs, 1985, 29, 455-473 and "Design of Prodrugs", ed. H. Bundgaard, Elsevier, 1985. Drugs having an amino group may be derivatised with a ketone or an aldehyde such as formaldehyde to form a Mannich base. This will hydrolyse with first order kinetics in aqueous solution. Pharmaceutically acceptable ester derivatives of the drugs in which one or more free hydroxy groups are esterified in the form of a pharmaceutically acceptable ester are particularly prodrug esters that may be convertible by solvolysis under physiological conditions to the drugs having free hydroxy groups.

Preferably, where a covalent interaction with the polymer of the invention is sought, the drug should be such that is carries a reactive function, such as a carboxyl, a hydroxyl, a thiol or an amino group. For instance, the drug may comprise an acidic functionality (propionic acid, carboxylic group, or an acetic acid carboxylic group) with a lipophilic tail composed by aryl derivatives. In this case, there is a chemical conjugation with the polymer network via degradable linkage. The linkage of the resorbable microspheres of the invention can be formed from a hydroxy and an acid group of an anticancer drug or a linker attached to such drug. Examples of anticancer agents: mitomycin, melphalan, methotrexate, raltirexed, gemcitabine, doxorubicine, irinotecan; example of NSAID: ibuprofen. The introduction of a hydrophilic units along the polymer chain using a hydrophilic monomer of formula IX as described above increases the drug release percentage (Babazadeh, Int J Pharm 316 (2006) 68).

In the chemically conjugated drug, the loading is predictable since it is directly connected to the chemistry of the particles. The release will occur by hydrolysis of the linker between the polymer network and the drug.

As indicated above, in particular where the polymer of the invention is obtained from the polymerization at least one charged, ionisable, hydrophilic, or hydrophobic monomer, the drug may also be loaded onto the polymer, that is be adsorbed on the polymer by non-covalent interactions. This particular way of entrapping drugs or prodrugs is called physical entrapment. No particular requirement is then imposed on the drug or prodrug to be loaded.

Loading may proceed by numerous methods well-known to one of skill in the art such as passive adsorption (swelling of the polymer into a drug solution) or by ionic interaction. Efficiency of encapsulation depends mainly of the compatibility between both structures and/or favourable interactions.

First Method: Adsorption of Drug by the Microsphere

The polymer according to the present invention, in particular when it forms a microspheres behave like dry sponges able to absorb passively drug solutions by swelling.

For instance, the polymer in a dry form, in particular in a freeze-dried form is made to swell in a solution containing a predetermined amount of the drug or the prodrug for 1 h to 24 h depending on the drug; the loaded polymer is then washed twice with a 0.9% (w/v) sodium chloride solution.

To improve the drug loading, non aqueous solvents such as DMF, DMSO, N-methylpyrrolidone, dimethylethylamide, diethylene glycol dimethyl ether, ethyl lactate, ethanol and methanol may be used to facilitate the dissolution of the drugs.

In order to adjust the hydrophilic/hydrophobic balance, when hydrophobic drug are to be loaded in the polymer, a hydrophilic comonomer of formula IX as defined above could be incorporated in the polymer network. To prevent the increase of degradation time, a more reactive crosslinker (more sensible to hydrolysis) could be also added. For example, a more reactive crosslinker consists in the one prepared in Example 1.2 below.

For example, the following drugs could be loaded in the polymer according to the present invention by this method: Sunitinib, Ibuprofen, Irinotecan, Cisplatin.

Second Method: Ionic Interactions

Several classes of therapeutic agents are positively or negatively charged at physiological pH. In this case, the type of polymer has an impact on the type of drug or prodrug that can be loaded.

If the polymer according to the present invention is anionic due to the use of an anionic monomer of formula V as described above in which E represents for example a carboxylate, sulfonate, sulphate or phosphate group, the drug to be loaded should be cationic, i.e. positively charged at physiological pH, such as doxorubicin and irinotecan to achieve high association or complexation efficiencies. Advantageously E represents a carboxyl group. Indeed carboxyl groups have the ability to form strong ionic interactions with desired drug candidates because they are excellent hydrogen bond donors.

Anionic polymers, owing to their high negative-charge density can bind substantial amounts of cationic drugs. The complex formed may in some cases improve the drug stability, but also facilitate its sustained drug release. The loading capacities and release of the drug are assessed by HPLC. Degradation rate of the polymeric network will be assessed as described by Vlugt-Wensink et al, biomacromolecules, 2006, 7, 2983-2990.

If the polymer according to the present invention is cationic due to the use of a cationic monomer of formula V as described above, the drug to be loaded should be anionic, i.e. negatively charged at physiological pH, to achieve high association or complexation efficiencies. Examples of anionic drug are ibuprofen (aryl propionate compound) or foscarnet (analog of pyrophosphate with anti-virus activity).

Drug release is assessed by HPLC and/or spectroscopic methods like UV. Degradation rate of the polymeric network will be assessed as described by Vlugt-Wensink et al, biomacromolecules, 2006, 7, 2983-2990.

Whatever the ionic charge introduced on the polymer network, the polymer will become softer and will be degraded more rapidly compared to its neutral analog. Since presence of ionic entities attracts water molecule inside the network, we should add an entity to repel them. Such entities are neutral hydrophobic monomers. Examples of neutral hydrophobic monomers are octyl or dodecyl methacrylates. Percentage and nature of the hydrolysable crosslinker may also be adjusted.

Third Method: Other Non Covalent Interaction

In order to increase the drug loading and control the rate of drug release, a concept consists to introduce certain chemical moieties into the polymer backbone that are capable of interacting with the drug via non covalent interactions. Examples of such interactions include electrostatic interactions (described above), hydrophobic interactions, π-π stacking, and hydrogen bonding, among others.

Hydrophobic Interaction/Host-guest Interaction in which the Host is a Cyclodextrin.

In this case E will be a cyclodextrin and in particular the monomer will have the formula (VI)

Because of the hydrophobic internal cavity of cyclodextrin, this molecule can either partially or entirely incorporate suitably sized lipophilic or hydrophobic low molecular weight drugs or prodrugs. Inclusion of such drugs or prodrugs into the cyclodextrin cage leads to a gain of entropy due to the formation of a stable complex. In general, the stronger the affinity constant of the drug: cyclodextrin, the slower the release is. This feature provides system suitable for sustained drug release (Biomaterials 2009, 30, 1348).

Cyclodextrins containing polymers have been proposed for drug loading more specifically for hydrophobic drugs (see for example WO2007072481).

Examples of (meth)acrylic structures bearing cyclodextrin residue are proposed in the following references: Macromol Chem Phys 2009, 210, 2107; Macromol Chem Phys 2010, 211, 245; J polym Sci 2009, 47, 4267.

The polymer according to the present invention can be loaded using this method with hydrophobic low molecular weight drugs like ibuprofen, indomethacin, coumarin, doxorubicin and irinotecan.

Hydrophobic Interaction/Host-guest Interaction in which the Host is a Crown Ether.

Crown ethers are cyclic compound which contain an internal hole or cavity. As such, their internal molecular void may be penetrated by various molecular species. In some cases, specific, stabilizing interactions were identified between the crown and the "partner" molecule, such as urea. Also, crown ethers can undergo association with metal complexes (Chulkova, Inorg Chem Commun 2010, 13, 580). So, such compounds are useful as drug delivery systems.

Examples of (meth)acrylic structures bearing crown ether residue are proposed in the following references: Polymer 2004, 45, 1467 Macromolecules 2003, 36, 1514.

The polymer according to the present invention can be loaded using this method with chemotherapeutics agent such as 5-fluorouracil, Cisplatin, Doxorubicin.

π-π Interactions

The monomer of formula IV may have a structure which allows π-π interactions with the drug or prodrug. This type of bonding is reported by Mahmud et al (macromolecules 2006, 39, 9419). In this case E is selected from the group constituted of a C5-C20 aryl group, a (5-30-members) heteroaryl group containing an heteroatom chosen in the group consisting of O, N or S, a O—C5-C20 aryl group and a O-(5-30-members) heteroaryl group. In particular, E can be chosen in the group consisting of benzene, naphtalene, anthracene, thiophene, aromatic amines like pyridine, carbazol, porphyrin and triphenylenes. Advantageously, the monomer will have the formula (VIII).

Examples of this type of monomer are 2-(4-benzoyl-3-hydroxyphenoxy)ethyl(meth)acrylate, 2-hydroxy-3-phenoxypropyl(meth)acrylate, ethylene glycol phenyl ether(meth) acrylate, benzyl methacrylate, naphtyl methacrylate, 9H-carbazole-9-ethylmethacrylate.

This polymer can be loaded with hydrophobic low molecular weight drugs such as 5-fluorouracil, doxorubicin, Indomethacin and ibuprofen.

H Bonding

H-bonds are ideal noncovalent interactions to favour drug encapsulation capability and control the drug release. H-bonds are formed when a donor (D) with an available acidic hydrogen atom is interacting with an acceptor (A) carrying available nonbonding electron lone pairs. The strength depends mainly on the solvent and number and sequence of the H-bond donors and acceptors. A wide variety of hydrogen bonding motifs have been reported in the literature which can be easily incorporate into polymer structures.

Whatever the choice of interaction to entrap the drug, chemical structure of the network will be adjust to conserve its properties (co-monomer, nature and percentage of crosslinker).

Besides, it is preferred that the drug as defined above is an anti-cancer drug or an NSAID.

Examples of suitable NSAIDs according to the invention encompass ibuprofen, ketoprofen, diclofenac, indomethacin or naproxen.

Examples of suitable anti-cancer drugs according to the invention encompass mitomycin, melphalan, methotrexate, raltirexed, gemcitabine, doxorubicine, or irinotecan.

More advantageously, the drug or the prodrug is chosen in the group consisting of anti-inflammatory agents, local anesthetics, analgesics, antibiotics, anticancer agents, tissue regeneration agents, oligosaccharides advantageously having a degree of polymerization (DP) of 3 to 10, steroid, and mixtures thereof, advantageously from the group consisting of lidocaine, bupivacaine, xylocalne, novocaine, benzocaine, prilocalne, ripivacaine, propofol, ibuprofen, ketoprofen, diclofenac, indomethacin, trimacinolone, dexamethasone, naproxen, mitomycin, melphalan, methotrexate, raltirexed, gemcitabine, tobramicin, doxorubicine, irinotecan, sunitinib, cis platin, 5-fluorouracil, mitomycine C, bacampicillin, chloramphenicol succinate, chloramphenicol succinate ester and coumarin.

In a particular embodiment, the drug or prodrug loaded in the polymer according to the present invention is in the form of nanoparticles loaded with the drug or prodrug with an average size lower than 1 μm, the nanoparticles being nanospheres or nanocapsules.

In this case, the nanoparticles loaded with a drug are absorbed on or entrapped in the network of the resorbable polymer according to the present invention to obtain a controlled and/or sustained release of the drugs.

This embodiment concerns drugs or prodrugs having a fragile structure and/or with no possible interaction with the polymer network according methods described above. First of all, the drug or prodrug will be encapsulated or otherwise incorporated in nanoparticles in order to protect the drugs or prodrugs or facilitate its incorporation in the final form of the polymer and to make it possible to obtain a controlled and/or sustained (prolonged) release of the drugs or prodrugs.

The nanoparticles are nanospheres or nanocapsules having an average size lower than 1 μm when measured by light scattering. They may have an aqueous core or a matricial core.

When the nanoparticles have an aqueous core, they are used to contain a hydrophilic drug or prodrug such as for example 5-Fluorouracil, Mitomycine C, Bacampicillin, Chloramphenicol succinate. In this case, the incorporation of the drugs or prodrugs in the nanocapsules is realized during the preparation of the nanoparticules which are themselves prepared by the double emulsion method (Pharm Res 15(2):

270-5 1998, J Control Release 75(1-2): 211-24, 2001, Crit Rev Ther Drug Carrier Syst. 2002; 19(2):99-134)

When the drug or prodrug is water-insoluble such as for example Chloramphenicol succinate ester, it is preferably incorporated in a nanosphere with a matricial core. In that case, the incorporation of the drug or prodrug is made during the preparation of the nanoparticles themselves. The nanoparticles are prepared according to known methods such as the one described by Vauthier C, Bouchemal K "Methods for the preparation and manufacture of polymeric nanoparticles" Pharm Res 2009 May; 26(5):1025-58.

The polymer from which the nanoparticles are made is preferably chosen among polylactic acid (polylactide), polyglycolic acid (polyglycolide), lactide-glycolide copolymers, lactide-glycolide-polyethyleneglycol copolymers, polyorthoesters, polyanhydrides, biodegradable block-copolymers, poly(esters), poly(butyrolactone), poly(valerolactone), poly(malic acid) and generally polylactones and the copolymers of each of one or more of these polymers.

Preferably, the nanoparticles are made of lactide-glycolide-polyethyleneglycol copolymers.

These polymers form nanoparticles which contain, or coat the drug or prodrug, or in which the drug or prodrug is embedded, thus delaying the release of the drug or prodrug.

In order to load the polymer according to the present invention with the nanoparticles containing the drug or prodrug, the polymer will be poured in a suspension of nanoparticles loaded with the drug or prodrug in water and the obtained suspension is freeze-dried.

Resorbable implant comprises a marker such as a dye for controlling its delivery from the syringe towards the hub of the catheter or needle, or an imaging agent for its visibility in the body during or after injection (barium sulphate, tungsten or titanium powder, iodinated compounds, paramagnetic compounds such as dextran-magnetite particles, Gadolinium derivatives, a radionucleide).

Form of the Polymer

Preferably, the polymer of the invention is in the form of a film, a foam, a particle, a lump, a thread, or a sponge, and most preferably is in the form of a spherical particle. The spherical particle is preferably a microsphere, i.e. has a diameter upon swelling (i.e. upon hydration), ranging from 1 to 5000 µm, more preferably ranging from 50 and 2500 µm, typically from 50 and 1000 µm (to be not phagocytised and pass easily through small needles), more advantageously ranging from 100 to 300 µm or from 300 to 500 µm, or from 500 to 700 µm, or from 700 to 900 µm, or from 900 to 1200 µm. The spherical particles should have a diameter small enough to be injected by needles or catheter, in particular small needles diameter but big enough to avoid engulfment by macrophage. The spherical particles can be injected after swelling. Their swelling could also be limited for example to about 50% of their total capacity of fluid absorption, before injection in order for them to swell mainly after implantation by absorbing physiological fluids such as the fluid from wounds, from interstitial medium and from blood fluids.

In order to swell, the polymer of the invention may absorb, preferably in a controlled way, liquids, such as water, in particular from solutions such as physiological saline, glucose solution, plasma, ionic or non ionic iodinated contrast media, iron oxide based contrast media for magnetic resonance imaging, drug solutions, buffered solution or any sterile apyrogen liquid that is injectable in the human or animal body and that are commonly used in embolization procedures or in operations of dermal filling or cavities, or in injections in natural cavities such as intraarticular spaces, brain ventricles, subarachnoidal space. A defined and limited quantity of water is absorbed by the polymer of the invention, thereby enabling, where the polymer is a spherical particle, to anticipate the diameter upon swelling.

Pharmaceutical and Therapeutical Use of the Polymer

Advantageously, the range which may be obtained for the polymer of the invention in the form of spherical particles makes it particularly suitable to block arterioles that are detectable by angiography and accessible by navigation to catheter and micro-catheters. Besides, the ability of the polymer of the invention to absorb contrast media, such as ionic or non ionic iodinated contrast media, iron oxide based contrast media for magnetic resonance imaging, barium sulphate, tungsten or tantalum, renders it particularly useful as a radio-opaque microsphere.

Advantageously also, resorption of the polymer of the invention depends on hydrolysis and not on an enzymatic mechanism. Resorption speed may thus be readily controlled by modulating the type and amount of bio-resorbable cross-linker and monomer as defined above. In particular due to the presence of ester linkage in the polymer network, the residue obtained after resorption have a low molecular weight and therefore do not accumulate in the kidney of the patient.

Equally advantageous, resorption of the polymer of the invention may range from a few hours to a few weeks or even a few months depending on the type and amount of bio-resorbable cross-linker and monomer as defined above. In addition, the polymer of the invention develops only a limited local inflammatory response upon implantation, since the degradation products of the polymer are non toxic and quickly eliminated.

The pharmaceutical composition thus defined contains a pharmaceutically acceptable carrier, advantageously intended for administration of the drug by injection.

Exemplary of pharmaceutically acceptable carrier includes but are not limited to water for injection, saline, starch, hydrogel, polyvinylpyrrolidone, polysaccharide, hyaluronic acid ester, and plasma. The pharmaceutical composition can also contain a buffering agent, a preservative, a gelling agent, a surfactant. Advantageously, the pharmaceutically acceptable carrier is saline or water for injection.

The pharmaceutical composition should have a viscosity acceptable for injection. In particular it could be of between 10 and 100 cP, more advantageously of between 20 and 30 cP when measured at 25° C. with Couette viscosimeter.

In particular the injectable pharmaceutical composition comprises
  (a) a polymer according to the present invention, loaded or non loaded with a drug, having a spherical shape of a diameter of between 50 and 500 µm upon total or limited swelling and a resorption time of between a two days to 3 weeks;
  (b) a polymer according to the present invention loaded or non loaded with a drug, having a spherical shape of a diameter of between 50 and 500 µm upon total or limited swelling and a resorption time of between one to 3 months; and
  (c) at least one pharmaceutically acceptable excipient.
In particular, the pharmaceutically excipients can be an hydrogel, for example having a resorption time of at most 1 week.

Advantageously the particles of polymer (a) and of polymer (b) have the same density.

In a particular advantageous embodiment, the spherical particles of polymer (a) and (b) have all the same diameter upon total or limited swelling, in particular chosen in the range of 100 to 300 μm or in the range of 300 to 500 μm, more advantageously in the range of 100 to 300 μm.

The proportion of polymer (a) and (b) in the pharmaceutical composition can be of between 20 to 80% by weight, advantageously of between 40 and 70% by weight, still more advantageously of 60% by weight.

In another advantageous embodiment, the proportion of polymer (a) is identical to the proportion of polymer (b) in the pharmaceutical composition.

In another advantageous embodiment, their proportions are differents. For example in this case, their respective ratio is: polymer (a) between 60 and 80%, advantageously 70% by weight, and polymer (b) between 20 and 40%, advantageously 30% by weight of the total amount of polymer (a)+(b).

In a particular embodiment, the spherical particles of polymer (a) and (b) do not have the same diameter. Advantageously the diameter of the spherical particles of polymer (a) is of between 100 and 300 μm and the diameter of the spherical particles of polymer (b) is of between 300 and 500 μm.

In another advantageous embodiment, the spherical particles of polymer (a) do not have all the same diameter. Some of them have a diameter of between 100 and 300 μm and the other a diameter of between 300 and 500 μm, advantageously half of them have a diameter of between 100 and 300 μm and the other half a diameter of between 300 and 500 μm, In a particular composition according to the present invention the spherical particles of polymer (a) and the spherical particles of polymer (b) have all a diameter of between 100 and 300 μm, the proportion of particles of polymer (a) being 70% by weight whereas the proportion of particles of polymer (b) is 30% by weight.

In another particular composition according to the present invention the spherical particles of polymer (a) and the spherical particles of polymer (b) have all a diameter of between 300 and 500 μm, the proportion of particles of polymer (a) being 70% by weight whereas the proportion of particles of polymer (b) is 30% by weight.

In a further particular composition according to the present invention the spherical particles of polymer (a) have all a diameter of between 100 and 300 μm, and the spherical particles of polymer (b) have all a diameter of between 300 and 500 μm, the proportion of particles of polymer (a) being 50% by weight whereas the proportion of particles of polymer (b) is 50% by weight.

In still a further particular composition according to the present invention, half of the spherical particles of polymer (a) have all a diameter of between 100 and 300 μm, the other half have all a diameter of between 300 and 500 μm and the spherical particles of polymer (b) have all a diameter of between 300 and 500 μm, the proportion of particles of polymer (a) being 50% by weight whereas the proportion of particles of polymer (b) is 50% by weight.

After injection this pharmaceutical composition forms a depot in the site of injection.

These compositions are particularly useful for filling of and/or camouflaging and/or correcting wrinkles, fine lines, skin cracks, cutaneous depressions, lipodystrophies, facial hemiatrophy, second branchial arch syndrome and/or scars, in particular acne scars and/or smoothing out irregularity of the skin and/or as a matrix for cellular culture and/or for tissue engineering. In fact, a large part of particles of polymer (a) is resorbed quickly in situ to promote tissue ingrowth in the depot. The resorption is progressive and develops in three phases to help the body to consider the depot as a matrix and not as a foreign body.

After injection there are three phases:

During the acute phase (a few days) the composition has a bulking effect. There is (controlled) water intake of the composition due to the swelling of the particles of polymer (a) and at a lesser degree of polymer (b). There is also proteins adsorption and cells adhesion on the implanted composition according to the present invention.

During the second phase (which last weeks or months) occurs the resorption of the particles of polymer (a), which creates a porosity of the bulk facilitating its penetration by cells (fibroblasts for example), beginning of collagen deposit and fibrosis (first network structure). The particles of polymer (a) are replaced by collagen or hyaluronic acid phase. These particles are designed to be very supple and behave as a viscous gel facilitating the injection and the stability of the particles of polymer (b). The proportion of these particles will be maintained relatively low in order to avoid a global inflammatory response directed towards the depot. In a third phase, during the next months, there is a resorption of the particles of polymer (b) which will open new channels for a total replacement by tissular growth and its vascularisation (fibrovascular ingrowth).

Due to this type of composition the porosity of the depot obtained after injection increases over time further to the resorption of the polymer according to the present invention. The rate and the importance of the resorption are controlled by the polymer used for preparation of the composition and therefore by their time of resorption. The time of resorption is dependent on the type of monomer used for the preparation of the polymer and in particular on the type and amount of the crosslinker.

Therefore, the polymer according to the present invention allows the obtention of injectable suspension of a combination of resorbable microspheres having various sizes and resorption times to produce in a controlled way in situ after implantation a tissue scaffold or matrix, which is transformed by resorption in a porous structure designed to be colonized by a tissue ingrowth.

The properties of the porous structure (pore size and connection, time of appearance) are designed by controlling several factors: nature of resorbable microspheres, proportions of the different resorbable microspheres associated in the suspension, sizes of the different resorbable microspheres.

In order to increase tissue ingrowth, the polymer according to the present invention can be loaded with drugs as described above. Advantageously, these drugs can be chosen in low molecular weight pro-angiogenic factors, in particular chosen in the group consisting of prostaglandins (PGE1, PGE2, PGF) and thyroxine (Lei, 121-132, 2004, Basic Research in Cardiology).

Advantageously, pro-angiogenic factors are chosen in the group consisting of oligosaccharides obtained from hyaluronic acid, composed between 3-10 disaccharides (Selvin, 58-68, 2007, Matrix biology).

To support cell adhesion and growth, peptides that enhance cell adhesion and spreading can be grafted on the polymer. Advantageously, ligands are chosen in the group consisting of RGD motif identified in extracellular molecules (fibronectin), IKVAV, YIGSR and RNIAEIIKDI peptides deduced from laminin (Tessmar and Göpferich, 274-291, 2007, Advanced Drug Delivery Reviews), or proteoglycan-binding peptides consisting of the sequence XBBXBX and XBBBXXBX, where B is a basic amino acid and X is a hydropathic amino acid as potential heparin-binding domains that bind cell surface proteoglycans (Rezania and Healy, 19-32, 1999, Biotechnol Prog). An example of proteoglycan-binding peptide is FHRRIKA motif. The easiest way to incorporate the adhesion sequences is the modification of the small peptides with double bond-containing acrylic acid derivatives (Tessmar and Göpferich, 274-291, 2007, Advanced Drug Delivery Reviews, Hern et Hubbell, 266-276, 1998).

The polymer according to the present invention is particularly suitable for the preparation of the pharmaceutical composition as described above in particular for its use for filling of and/or camouflaging and/or correcting wrinkles, fine lines, skin cracks, cutaneous depressions, lipodystrophies, facial hemiatrophy, second branchial arch syndrome and/or scars, in particular acne scars and/or smoothing out irregularity of the skin and/or as a matrix for cellular culture and/or for tissue engineering. However even if it is less suitable the polymer described in ° PCT/EP 2010/063227 can also be used for this type of application and for preparing a pharmaceutical composition as described above.

The present invention also concerns an implant, in particular for implantation into tissues, advantageously facial tissue, in particular soft tissues, internal anatomical spaces, such as peritoneum and meningeal spaces, body cavities, ducts and vessels, containing the composition as described above or the polymer according to the present invention.

Depending on the type of the intended therapeutical or cosmetic application, the site of application is different. If the intended application concerns the face, the implant is injected in the soft tissue, in particular subcutaneously or intradermally.

If the implant is injected in the tissue, it can increase the tissue volume.

In a particular embodiment, the pharmaceutical composition comprises the polymer of the invention in a dry form, such as a lyophilized form.

The pharmaceutical composition of the invention and/or the polymer according to the present invention will be preferably used in the frame of embolization, in particular for uterine artery embolization (UAE), or for haemostasis. In embolization, the polymer of the invention need not comprise drugs or be loaded with drugs. It can also be used in the treatment of arteriovenous malformations, cerebral aneurysm, gastrointestinal bleeding, epistaxis, primary post-partum haemorrhage and/or surgical haemorrhage The pharmaceutical composition of the invention is also preferably used for treating cancer. In this case, treatment may occur by embolization, in particular by repeated embolization, and/or by delivery of anti-cancer drugs or prodrugs comprised in the polymer of the invention or loaded on the polymer of the invention. In particular the cancer of interest is chosen in the group consisting of liver lesions, typically hepatocellular carcinoma (HCC), kidney lesions and/or uterine fibroids. In these cases the pharmaceutical composition can advantageously be injected in the tumor site by direct intra or peri tumoral injection, or by means of selective catheterisation and embolisation.

Besides, the pharmaceutical composition of the invention may be preferably used for preventing or treating inflammation. In this case, it is preferred that the polymer of the invention comprises NSAIDs or be loaded by NSAIDs. In particular, the pharmaceutical composition of the invention is particularly suited for preventing or treating inflammation associated with:
  joints cavities, tendons, cartilage, and bone defects;
  operative cavities after surgery of brain, in maxillar bone after teeth extraction, in bone after resections, in liver or kidney after surgical tumor resection;
  muscles, in particular in cases of myositis or rupture;
  cerebrospinal fluid cavities in the central nervous system;
  joint surgery, arthroscopy, intrarticular lavage, menisectomy, osteotomy.

The present invention also concerns the use of the implant as described above, of the polymer according to the present invention or of the composition as described above for filling of and/or camouflaging and/or correcting wrinkles, fine lines, skin cracks, cutaneous depressions, lipodystrophies, facial hemiatrophy, second branchial arch syndrome and/or scars, in particular acne scars and/or smoothing out irregularity of the skin and/or as a matrix for cellular culture and/or for tissue engineering.

It concerns also the implant as described above or polymer according to the present invention or a composition as described above for use as a medicament, advantageously intended for the prevention of skin ageing and/or for wound healing and/or for tissular reconstruction and/or for soft tissue repair, for regenerating tissue in an animal, in particular in humans. However even if it is less suitable the polymer described in ° PCT/EP 2010/063227 can also be used for this type of application.

In a particular aspect of the invention, it is possible to use the polymer and/or the composition and/or the implant according to the invention as a matrix for cellular culture, with applications in particular in cosmetic surgery, dermatology, rheumatology and gastroenterology. Actually, the resorbable polymer according to the invention, in particular in the form of the composition as described above, is a good three-dimensional substrate for supporting the growth of various types of cells. However even if it is less suitable the polymer described in ° PCT/EP 2010/063227 can also be used for this type of application.

In cosmetic surgery, it is possible to cite applications for implants for filling in wrinkles or hollows.

In dermatology, it can be used for healing chronic wounds: as a matrix, it makes possible the tangential development of the process of healing and the prevention of budding in the case of hypertrophic healing.

In rheumatology and orthopedics, the use of the polymer and/or the composition and/or the implant according to the invention as a matrix for the cellular culture is particularly suitable for the repair of the cartilage by chondroinduction.

Relative to the applications of the polymer and/or the composition and/or the implant according to the invention as a three-dimensional substrate for the cellular growth of autologous cells is particularly suitable for preparing tissue engineered implantable scaffolds for bone, cartilage, skin, and other organs reconstruction. However even if it is less suitable the polymer described in ° PCT/EP 2010/063227 can also be used for this type of application.

The polymer and/or the composition and/or the implant according to the present invention can also be used for variety of soft tissue repair and augmentation procedure, in particular on the facial tissue such as for example camouflaging scars, filling depressions, smoothing out irregularity, correcting asymmetry in facial hemiatrophy, second branchial arch syndrome, facial lipodystrophy and camouflaging age-related wrinkles. It can be used in reconstructive surgery to restore form and/or function to soft tissues altered by age, trauma, disease, or other defect. It can also replace facial fat loss (lipoatrophy), for example, to provide volume in areas of the patient's soft tissues which suffer from fat, collagen or muscle loss for reasons of old age or disease. However even if it is less suitable the polymer described in ° PCT/EP 2010/063227 can also be used for this type of application.

Definition

As used herein, the term "alkyl" refers to a straight or branched saturated monovalent hydrocarbon radical, having the number of carbon atoms as indicated. For example, the term "$C_{1-6}$-alkyl" includes $C_1$, $C_2$, $C_3$, $C_4$, $C_6$, and $C_6$ alkyl groups. By way of non-limiting example, suitable alkyl groups include methyl, ethyl, propyl, iso-propyl, butyl, iso-butyl, tert-butyl, pentyl and hexyl. In one aspect of the present invention ranges of alkyl groups are: $C_{1-6}$-alkyl, $C_{1-4}$-alkyl, $C_{1-3}$-alkyl and $C_{1-2}$-alkyl.

As used herein, the term "aryl" refers to monovalent unsaturated aromatic carbocyclic radical having one, two, or three rings, which may be fused or bicyclic. In one aspect of the present invention, the term "aryl" refers to an aromatic monocyclic ring containing 5 or 6 carbon atoms, an aromatic bicyclic or fused ring system containing 7, 8, 9 or 10 carbon atoms, or an aromatic tricyclic ring system containing up to 10 carbon atoms. By way of non-limiting example, suitable aryl groups include phenyl, biphenyl, anthracenyl, thiophenyl. In one aspect of the present invention ranges of aryl groups are: $C_{5-20}$-aryl, $C_{5-10}$-aryl, $C_{5-8}$-aryl and $C_{6-7}$-aryl.

The term "(5-30members)heteroaryl" refers to monovalent unsaturated aromatic heterocyclic radicals containing 5 to 30 members having one, two, three or more rings containing at least one hetereoatom, in particular O, N or S, advantageously two heteroatoms, in particular 3 heteroatoms, which may be fused or bicyclic. Suitably, the term "heteroaryl" encompasses heteroaryl moieties that are aromatic monocyclic ring systems containing five members of which at least one member is a N, O or S atom and which optionally contains one, two or three additional N atoms, an aromatic monocyclic ring having six members of which one, two or three members are a N atom, aromatic bicyclic or fused rings having nine members of which at least one member is a N, O or S atom and which optionally contains one, two or three additional N atoms or aromatic bicyclic rings having ten members of which one, two or three members are a N atom. By way of non-limiting example, suitable heteroaryl groups include furanyl, pyridyl, phthalimido, thiophenyl, pyrrolyl, imidazolyl, pyrazolyl, thiazolyl, isothiazolyl, oxazolyl, oxadiazolyl, pyronyl, pyrazinyl, tetrazolyl, thionaphthyl, benzofuranyl, indolyl, oxyindolyl, isoindolyl, indazolyl, indolinyl, azaindolyl, benzopyranyl, coumarinyl, isocoumarinyl, quinolyl, isoquinolyl, cinnolinyl, quinazolinyl, benzoxazinyl, chromenyl, chromanyl, isochromanyl, thiazolyl, isoxazolyl, isoxazolonyl, isothiazolyl, triazolyl, oxadiazolyl, thiadiazolyl, triazyl carbazol, porphyrin, triphenylenes and pyridazyl, advantageously pyridine, carbazol, porphyrin, triphenylenes.

EXAMPLES

Example 1

1. Synthesis of the Bio-Resorbable Cross-Linker by the HEMA/PEGMA method

First Step:
In a dry schlenk containing a magnetic stirring bar, lactide (2.22 g; 0.0154 mol) and hydroxyethyl methacrylate (0.75 mL; 0.0062 mol) were dissolved in 5 ml of toluene under nitrogen. The reaction was initiated by introducing a toluene solution of Sn(Oct)$_2$ (8 mg) into the above system. After 20 h at 90° C., 5 ml of chloroform was added to dilute the reaction mixture and the formed polymer was purified by precipitating in a large volume of petroleum ether. Yield 94%.

$^1$H NMR in CD$_3$COCD$_3$: 1.53 (m, CH$_3$, PLA), 1.91 (s, CH$_3$, methacrylate), 4.38 (m, CH$_2$, HEMA), 5.17 (m, CH, PLA), 5.65-6.10 (m, CH$_2$=C).

Second Step:
The polymer formed in the first step was further modified through the hydroxyl group at the end of PLA chain by reacting with methacryloyl chloride. The preformed polymer (1.07 mmol of OH group, 1 eq.) was dissolved in anhydrous CH$_2$Cl$_2$ (2.5 ml) in a three necked flask equipped with magnetic stirrer and a dropping funnel. The content of the flask was cooled to 0° C. and triethylamine (1.5 eq.; 0.0016 mol) was added. The solution was stirred and then methacryloyl chloride (1.5 eq.; 0.0016 mol) in CH$_2$Cl$_2$ (2.5 ml) was added dropwise to the solution. The stirring was continued 1 h at 0° C. and then one night at room temperature. The triethylamine salt was removed by filtration and the polymer was precipitated in a large volume of petroleum ether. Yield: 95%.

$^1$H NMR in CD$_3$COCD$_3$: 1.53 (m, CH$_3$, PLA), 1.91 (m, CH$_3$, methacrylate), 4.39 (m, CH$_2$, HEMA), 5.17 (m, CH, PLA), 5.65-6.16 (m, CH$_2$=C).

2. Synthesis of The Bio-Resorbable Cross-Linker by The PEG Method

First Step:
In a dry schlenk containing a magnetic stirring bar, the PEG600 (10 g; 0.0167 mol) was reacted with d,l-lactide (7.2 g; 0.05 mol) and glycolide (5.8 g; 0.05 mol) for 20 h at 115° C. using stannous octoate as catalyst (114 mg) under argon. Then, the polymer was dissolved in chloroform, precipitated in a large volume of petroleum ether/diethyl ether (50/50) then in pure petroleum ether.

$^1$H NMR in CDCl$_3$: 1.55 (m, CH$_3$, PLA), 3.64 (m, CH$_2$, PEG), 4.25 (m, CH$_2$, PEG), 4.80 (m, CH$_2$, PGA), 5.20 (m, CH, PLA)

Second Step:
The polymer formed in the first step was further modified through the hydroxyl groups at the end of PLGA by reacting with methacrylic anhydride. In a typical reaction, the preformed polymer (4.91 g) was dissolved in degased ethyl acetate (25 ml) in a dry Schlenk tube equipped with magnetic stirrer. The content of the flask was cooled to 0° C. and methacrylic anhydride (3.3 ml.; 0.022 mol) was added dropwise to the solution under an argon flow. The stirring was continued 1 h at 0° C. and then 6 h at 80° C. After cooling, the polymer was precipitated three times in a large volume of petroleum ether.

$^1$H NMR in CDCl$_3$: 1.56 (m, CH$_3$, PLA), 1.94 (m, CH$_3$, methacrylate), 3.63 (m, CH$_2$, PEG), 4.29 (m, CH$_2$, PEG), 4.80 (m, CH$_2$, PGA), 5.20 (m, CH, PLA), 5.64-6.15 (m, CH$_2$=C)

A series of bio-resorbable crosslinkers has been synthesized by varying the molecular weight of the PEG, and the length and the chemical composition of the resorbable segment (Table 1).

TABLE 1

| Resorbable crosslinkers | | | |
| --- | --- | --- | --- |
| Code | PEG (g · mol$^{-1}$) | Lact/glyc (mol %) | PD$_{res\ segment}$* |
| EG-PLGA$_{12}$ | 44 | 50/50 | 12 |
| TEG-PLGA$_{12}$ | 176 | 50/50 | 12 |

TABLE 1-continued

Resorbable crosslinkers

| Code | PEG (g·mol$^{-1}$) | Lact/glyc (mol %) | PD$_{res\ segment}$* |
|---|---|---|---|
| TEG-PLGA$_{20}$ | 176 | 50/50 | 20 |
| TEG-PLA$_{12}$ | 176 | 100/0 | 12 |
| PEG$_{13}$PLGA$_{12}$ | 600 | 50/50 | 12 |
| PEG$_{13}$PLA$_{12}$ | 600 | 100/0 | 12 |
| PEG$_{22}$PLGA$_{12}$ | 1000 | 50/50 | 12 |
| PEG$_{22}$PLGA$_{8}$ | 1000 | 50/50 | 8 |
| PEG$_{13}$PLA$_{12}$ | 1000 | 100/0 | 12 |
| PEG$_{13}$PCL$_{6}$ | 600 | PCL100 | 6 |

*polymerization degree of resorbable segment of resorbable crosslinkers

Example 2

Synthesis of 2-methylene-1,3-dioxepane (MDO)

The synthesis was performed using a modified method previously described by Undin and al (J PolymSci: Part A 48, 4965-4973-2010).

Step 1. A 1:1 molar ratio of 1,4-butanediol and bromoacetaldehyde diethylacetal was weighted into a round bottom flask together with Dowex 50 (2.5 g Dowex 50/mol of monomer). The reaction flask was fitted with a 10 cm vigreux column and heated to 100° C. at reduced pressure. The reaction was stopped when no more ethanol was distilled off. The product was purified by vacuum distillation at 100° C. Yield: 60%. $^1$H NMR (300 MHz, CDCl$_3$): 4.88 (t, 1H, CH), 3.93-3.62 (m, 4H, CH$_2$—O), 3.30 (d, 2H, CH$_2$Br), 1.70 (m, 4H, CH$_2$—CH$_2$—O).

Step 2. 2-(bromomethyl)-1,3-dioxepane (premonomer) were dissolved in 1/3 THF (3.2 ml anhydrous THF/g premonomer). Potassium tert-butoxide (2 mol equivalents compared with premonomer) and Aliquat 336 (2% mol compared with premonomer) was suspended in 2/3 THF into a round bottom flask, with a magnetic stirring bar, and cooled to 0° C. The solution of premonomer in THF was added drop by drop. The reaction was allowed to proceed at 0° C. for 3 h and at 25° C. for 12 h. After elimination of solid residue by centrifugation, the solvent was removed and the product was purified by vacuum distillation at 50° C. Yield: 57%. $^1$H NMR (300 MHz, CDCl$_3$): 3.92 (m, 4H, CH$_2$—O), 3.44 (s, 2H, =CH$_2$), 1.73 ppm (m, 4H, CH$_2$—CH$_2$—O).

Example 3

Synthesis of Ibuprofen Monomers

1. HEMA-iBu:

The following reaction was performed:

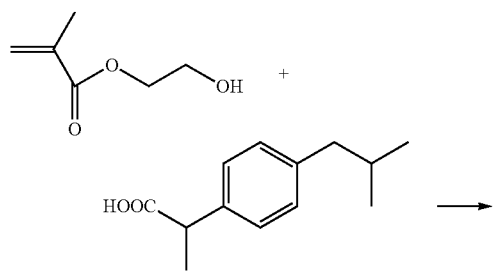

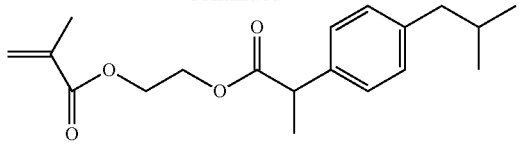

In a round bottom flask containing a magnetic stirring bar, ibuprofen (0.34 g; 1.65 mmol) and 4-Dimethylaminopyridine (0.01 g; 0.09 mmol) were solubilized in dry CH$_2$Cl$_2$ (4 ml) under nitrogen atmosphere. Hydroxyethyl methacrylate (0.21 g; 1.65 mmol) and a mixture of dicyclohexylcarbodiimide (0.34 g; 1.65 mmol) dissolved in 2 ml of dry CH$_2$Cl$_2$ were sequentially added at 0° C. After reacting 24 h at 0° C., the mixture was filtrate and the crude product was purified on silica gel column (cyclohexane/ethyl acetate: 2/1).

Characterization by $^1$H NMR in CD$_3$COCD$_3$: 0.88 (d, CH$_3$, isopropyl), 1.43 (d, CH$_3$—CH, ibuprofen), 1.85 (m, CH$_3$, methacrylate+CH-iPr, ibuprofen), 2.44 (d, CH$_2$-phenyl, ibuprofen), 3.75 (q, phenyl-CH—COO—, ibuprofen), 4.31 (m, CH$_2$, HEMA), 5.59-5.98 (m, CH$_2$=C), 7.16 (dd, C$_6$H$_4$)

2. GMA-iBu

The following reaction was performed:

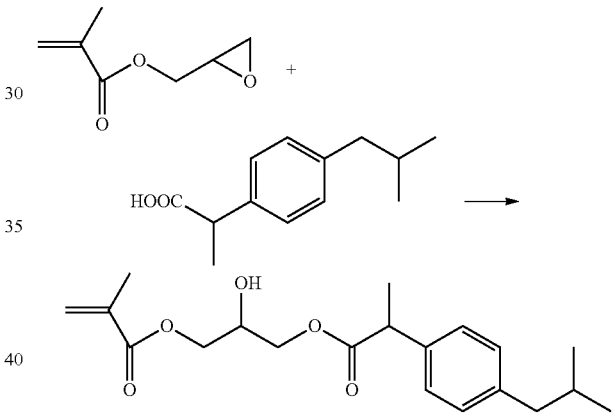

Glycidyl methacrylate (1.348 g; 9.5 mmol), ibuprofen (1.955 g; 9.5 mmol), hydroquinone (0.2 g) and pyridine (2 ml) were dissolved in 5 ml of DMF. The mixture was shaken under vacuum at 40° C. for 6 h. Then, the mixture was cooled and poured in aqueous saturated NaHCO$_3$ solution (20 ml). The organic phase was extracted three times by ethyl acetate, washed with saturated NaCl solution, dried on MgSO$_4$ and the solvent evaporated under reduced pressure. The residue was purified by chromatography (ethyl acetate/cyclohexane: 1/5). Yield: 40%.

Characterization by $^1$H NMR in CDCl$_3$: 0.89 (d, CH$_3$, isopropyl), 1.51 (d, CH$_3$—CH, ibuprofen), 1.85 (m, CH-iPr, ibuprofen), 1.94 (s, CH$_3$, methacrylate), 2.45 (d, CH$_2$-phenyl, ibuprofen), 3.75 (q, phenyl-CH—COO—, ibuprofen), 4.08-4.19 (m, CH$_2$—CH(OH)—CH$_2$), 5.60-6.12 (m, CH$_2$=C), 7.16 (dd, C$_6$H$_4$)

Example 4

Synthesis of Resorbable Hydrogels

1. In Organic Solvent

Resorbable crosslinker PEG$_{22}$PLGA$_{12}$ (5% mol) was dissolved in 1 ml toluene and degased under nitrogen. To this were added poly(ethylene glycol) methyl ether methacrylate Mw 300, 2-methylene-1,3-dioxepane and hexanethiol (3% mol/mol of PEGMA). 1% mol of AIBN were dissolved in 1 ml of toluene and added to the monomers solution. The mixture was heated at 80° C. for 8 h. After cooling, the polymer was washed twice with acetone and then distilled water.

Hydrogel discs (7 mm thickness and 21 mm diameter) were placed in a glass vial containing 50 ml of NaOH 0.1 N at 37° C. under agitation until total degradation (absence of solid residue). After one night, the content was dialysed to Milli-Q-water (molecular weight cutoff of 100-500 Da to remove lactic acid, glycolic acid and salts) and freeze-dried. The molecular weight of the residual polymer was determined by size exclusion chromatography after methylation of carboxylic groups (Table 2).

TABLE 2

Hydrogels prepared in toluene

| | $PEG_{22}PLGA_{12}$ (% mol) | PEG300MA (% mol) | MDO (% mol) | Mn of degradation products (kDa) |
|---|---|---|---|---|
| G#1 | 5 | 95 | 0 | 61 |
| G#2 | 5 | 90 | 5 | 31 |
| G#3 | 5 | 85 | 10 | 24 |
| G#4 | 5 | 75 | 20 | 6 |
| G#5 | 5 | 65 | 30 | 4 |
| G#6 | 5 | 55 | 40 | 4 |

The addition of the cyclic monomer having an exo methylene group, even at a low percentage, reduces the molecular weight of the residual polymer chain. After degradation, it is important to note that, whatever the percentage of MDO used, all the methacrylate chains in the degradation products have relatively low molecular weights, in the range of 4-30 kDa which is smaller than the molecular weight range that leads to accumulation in the circulatory system.

2. In Aqueous Solvent G#7

Resorbable crosslinker $PEG_{22}PLGA_8$ (0.33 g, 0.2 mmol) was dissolved in 3 ml distilled water and degased under nitrogen. To this were added poly(ethylene glycol) methyl ether methacrylate Mw 475 (1.8 g, 3.8 mmol), 2-methylene-1,3-dioxepane (0.023 g, 0.2 mmol), tetramethylethylenediamine (12 µl) and thioglycolic acid (10 mg). 180 mg of ammonium peroxodisulfate were dissolved in 0.2 ml of distilled water and added to the monomers solution. The mixture was heated at 40° C. for 30 min. After cooling, the polymer was washed with distilled water and freeze-dried.

Hydrogel discs G#7 (4 mm thickness and 10 mm diameter) placed in glass vial containing 10 ml of NaOH 0.1N were totally degraded (absence of visible residue) in 10 min.

Example 5

Resorbable Microspheres

1. Preparation of Resorbable Microspheres

A 0.5% of aqueous solution of 88% hydrolyzed polyvinylalcohol (120 ml) containing 3% NaCl was introduced into a 250 ml reactor and allowed to stand under a nitrogen atmosphere for 15 min. The monomer phase containing poly(ethylene glycol) methyl ether methacrylate, 2-methylene-1,3-dioxepane, resorbable cross-linker, chain transfer agent (3% mol/mol of PEGMA) and 1 mol % AIBN solubilised in 7.5 ml of toluene was degassed by bubbling nitrogen through the solution for 15 min. The monomer phase was added to the aqueous phase at 80° C. and stirred for 8 h. The mixture was filtered hot and washed with acetone and water. Then, beads were freeze-dried.

A series of resorbable microspheres has been synthesized by varying the nature of crosslinker, the PEG monomer and the percentage of MDO (Table 3).

TABLE 3

Resorbable Microspheres: Rate of degradation, and Mn of the degradation products

| | Crosslinker (% mol) | PEGMA (% mol) | MDO (% mol) | Weight loss[a,b] | Mn (kDa)[c] |
|---|---|---|---|---|---|
| MS#1 | $PEG_{13}PLGA_{12}$ (3%) | DEGMA - 97% | 0 | 23% at 1 month 100% at 4 months | |
| MS#2 | $PEG_{13}PLGA_{12}$ (5%) | PEGMA300 - 95% | 0 | 20% at 8 h 80% at 24 h | |
| MS#3 | $PEG_{13}PLA_{12}$ (5%) | PEGMA300 - 95% | 0 | 80% at 4 days 100% at 7 days | |
| MS#4 | $PEG_{22}PLGA_{12}$ (5%) | PEGMA300 - 95% | 0 | 26% at 8 h 100% at 24 h | 55 |
| MS#5 | $PEG_{22}PLGA_{12}$ (5%) | PEGMA300 - 92.5% | 2.5 | 100% at 24 h | 46 |
| MS#6 | $PEG_{22}PLGA_{12}$ (5%) | PEGMA300 - 90% | 5 | 100% at 24 h | |
| MS#7 | $PEG_{22}PLGA_{12}$ (5%) | PEGMA300 - 85% | 10 | 100% at 24 h | |
| MS#8 | $PEG_{22}PLGA_{12}$ (5%) | PEGMA300 - 75% | 20 | 100% at 24 h | 27 |
| MS#9 | $PEG_{22}PLGA_{12}$ (5%) | PEGMA300 - 65% | 30 | 100% at 48 h | 15 |

[a]PBS, pH7.4 at 37° C.
[b]Weight loss (%) = (W0 − Wt)/W0 × 100 where W0 and Wt are the dry weight of the sample before and after degradation, respectively.
[c]Molecular weight of the polymer chain after degradation Addition of a cyclic monomer having an exo methylene group does not prevent the suspension polymerization whatever its percentage and the nature of crosslinker/monomer. Moreover, the cyclic monomer reduces the molecular weight of the residual polymer chain after degradation.

The in vitro degradation rate of the microspheres listed above (Table 3) can be adjusted from less than 1 day to up to 4 months by varying the chemical composition of crosslinker and/or the nature of the PEG monomer. The PLA based crosslinkers lead to slower microsphere degradation rate than the PLGA ones. The length of the PEG segment of the crosslinker influences the resorption speed. The cyclic monomer does not notably modify the resorption speed.

2. Control of Size

It is entirely possible to achieve sharp size distributions through a remarkable range of particle sizes by simply varying the stirring speed, the ratio of water to monomer phase, and concentration of polyvinyl alcohol stabilizer. Particle size distribution was determined by laser diffraction on a Mastersizer S apparatus (Malvern Instrument Ltd.) at 25° C. Dry beads were dispersed in water and were allowed to swell for 15 min before measurement. Each injection was analyzed 3 times.

Combination of these factors permits the preparation of size ranges averaging from 220 µm (260 rpm, O/W=1/11), to 317 µm (215 rpm, O/W=1/8), to 614 µm (160 rpm, O/W=1/6) and to 1144 µm (120 rpm, O/W=1/6).

3. Injection of Microspheres Trough Needles Having Various Diameters

Dry microspheres (500-800 µm) were hydrated with saline (0.9 wt % NaCl in distilled water) and diluted at 50% with Omnipaque to form a test solution. Microsphere suspensions were then injected through short (I.V.) catheter with decreasing diameters (Table 4).

TABLE 4

Injection of microspheres

| Needles (Internal diameter µm) | MS#4 MDO (0%) | MS#7 MDO (10%) |
|---|---|---|
| 16G (1200 µm) | No resistance Absence of MS fragments | No resistance Absence of MS fragments |
| 18G (900 µm) | No resistance Absence of MS fragments | No resistance Absence of MS fragments |
| 20G (700 µm) | No resistance Absence of MS fragments | No resistance Absence of MS fragments |
| 22G (550 µm) | No resistance Absence of MS fragments | No resistance Absence of MS fragments |
| 24G (450 µm) | Low resistance Absence of MS fragments | Low resistance Absence of MS fragments |

The addition of a cyclic monomer having an exo methylene group in the polymer network does not modify the ability of microspheres to be injected through needles with decreasing diameters. The mechanical properties have not been modified by the introduction of the cyclic monomer.

Example 6

Synthesis of Ionic Resorbable Microspheres

The same procedure was used as in example 5, but an ionic monomer has been added in the toluene phase (Table 5).

TABLE 5 ionic Resorbable Microspheres: Rate of degradation

| | Ionic Monomer | Mol % ionic Monomer | Crosslinker[a]/ monomer | MDO (% mol) | Weight loss[b,c] |
|---|---|---|---|---|---|
| MS#10 | β-Carboxy ethyl acrylate | 10 | $PEG_{13}$-$PLGA_{12}$/ PEGMA300 | 0 | 100% at 24 h |
| MS#11 | Methacrylic acid | 10 | $PEG_{13}$-$PLGA_{12}$/ DEGMA | 0 | 98% at 14 days |
| MS#12 | Methacrylic acid | 10 | $PEG_{13}$-$PLA_{12}$/ PEGMA300 | 0 | 100% at 7 days |
| MS#13 | Methacrylic acid | 10 | $PEG_{13}$-$PLGA_{12}$/ PEGMA300 | 0 | 95% at 24 h |
| MS#14 | Methacrylic acid | 10 | $PEG_{22}$-$PLGA_{12}$/ PEGMA300 | 5 | 100% at 24 h |
| MS#15 | Methacrylic acid | 20 | $PEG_{13}$-$PLGA_{12}$/ PEGMA300 | 2.5 | 100% at 24 h |
| MS#16 | Methacrylic acid | 50 | $PEG_{22}$-$PLGA_{12}$/ PEGMA300 | 5 | 100% at 12 h |

[a] microspheres prepared with 3 or 5% mol crosslinker
[b] PBS, pH7.4 at 37° C.
[c] Weight loss (%) = (W0 − Wt)/W0 × 100 where W0 and Wt are the dry weight of the sample before and after degradation, respectively.

Microspheres with various amounts of ionic monomer have been synthesised successfully in presence or not of cyclic monomer. Their degradation rates are faster than the neutral microspheres for a similar composition and increased with the amount of ionic monomer. The cyclic monomer does not notably modify the resorption speed.

Example 7

Synthesis of Resorbable Hydrogels Containing Cyclodextrins

1. Preparation of Monomethacrylate β-cyclodextrin

The monomer was synthesized similar to a method previously described (Ren et al. Journal of polymer science, part A 2009, 4267-4278).

Step 1. yield=51%. $^1$H NMR (300 MHz, DMSO-$d_6$): 7.74 (d, 2H, tosyl), 7.45 (d, 2H, tosyl), 4.84-4.77 (m, 7H, O—CH—O), 3.70-3.45 (m, 28H), 3.40-3.20 (m, 14H), 2.43 (s, 3H, Ph-$CH_3$)

Step 2. yield=69% $^1$H NMR (300 MHz, $D_2O$): 9.26 (s, CHO), 5.20-5.10 (m, 7H, O—CH—O), 4.04-3.90 (m, 26H), ☐3.73-3.60 (m, 14H)

Step 3. yield=71%. $^1$H NMR (300 MHz, $D_2O$): 6.22 (s, =CH), 5.89 (s, =CH), 5.11 (d, 7H, O—CH-0), 4.04-3.88 (m, 28H), 3.71-3.59 (m, 14H), 3.05 (s, 2H, $CH_2$—OCO), 2.90 (s, 2H, $CH_2$—NH), 2.04 (s, 3H, $CH_3$—C=)

2. Preparation of Resorbable Hydrogels with Monomethacrylate β-cyclodextrin G#8

The monomethacrylate β-cyclodextrin was first solubilised in 4.5 ml of distilled water/DMSO (3/1 vol). To this were added in this order resorbable crosslinker $PEG_{22}$-$PLGA_8$ (0.33 g, 0.2 mmol), poly(ethylene glycol) methyl ether methacrylate Mw 475 (1.71 g, 3.6 mmol), 2-methylene-1,3-dioxepane (0.023 g, 0.2 mmol), tetramethylethylenediamine (12 µl) and thioglycolic acid (10 mg). 180 mg of ammonium peroxodisulfate were dissolved in 0.5 ml of distilled water and added to the monomers solution. The mixture was heated at 40° C. for 30 min. After cooling, the polymer was washed with distilled water and freeze-dried.

Hydrogel discs G#8 (4 mm thickness and 10 mm diameter) placed in glass vial containing 10 ml of NaOH 0.1N were totally degraded (absence of visible residue) in 10 min.

Addition of a cyclic monomer having an exo methylene group thus does not prevent the polymerization of the monomethacrylate cyclodextrin.

Example 8

Synthesis of Resorbable Hydrogels Containing Crown Ether

1. Preparation of 18-crown-6-methacrylate 2-hydroxymethyl-18-crown-6 (1 mmol) was dissolved in degased $CH_2Cl_2$ (10 mL) in a Schlenk tube equipped with magnetic stirrer. The content of the flask was cooled to 0° C. and triethylamine (3 mmol) was added. The solution was stirred and then methacryloyl chloride (3 mmol) was added dropwise to the solution. The stirring was continued 2H at 0° C. and then overnight at room temperature. The reaction mixture was extracted with 1M HCl solution, washed with water then saturated $Na_2CO_3$ solution and dried over $MgSO_4$. After filtration and evaporation of solvent, the residue was purified by chromatography on silica gel ($CHCl_3$/MeOH 9/1 eluent) to obtain 194 mg (yield 54%) of 2-methylmethacrylate-18-crown-6. $^1$H NMR (300 MHz, $CDCl_3$): 6.11 (s, 1H, =$CH_2$), 5.57 (s, 1H, =$CH_2$), 4.32-4.15 (m, 2H, $CH_2$—OCO), 3.81-3.68 (m, 23H, $CH_2$—O), 1.95 (s, 3H, $CH_3$)

2. Preparation of Resorbable Hydrogels with Crown Ether G#9 (30%), G#10 (50%)

Resorbable crosslinker $PEG_{22}$-$PLGA_{12}$ (0.22 g, 0.125 mmol) was dissolved in 0.8 ml toluene and degased under nitrogen. To this were added crown ether methacrylate (0.27 g, 0.75 mmol), poly(ethylene glycol) methyl ether methacrylate Mw 300 (0.49 g, 1.62 mmol), 2-methylene-1,3-dioxepane (14.3 mg, 0.125 mmol) and hexanethiol (7 µl). 2% mol of AlBN were dissolved in 0.2 ml of toluene and added to the monomers solution. The mixture was heated at 80° C. for 8 h. After cooling, the polymer was washed twice with acetone and then distilled water.

Hydrogel discs (4 mm thickness and 10 mm diameter) placed in glass vial containing 10 ml of NaOH 0.1 N were totally degraded (absence of solid residue) in 12 h.

Addition of a cyclic monomer having an exo methylene group thus does not prevent the polymerization of the crown ether methacrylate at different percentages.

Example 9

Synthesis of Resorbable Hydrogels Containing Naphtyl Groups

Resorbable crosslinker $PEG_{22}$-$PLGA_{12}$ (5% mol) was dissolved in 1.5 ml toluene and degassed under nitrogen. To this were added naphtyl methacrylate (naphtylMA), poly(ethylene glycol) methyl ether methacrylate Mw 300, 2-methylene-1,3-dioxepane (5 mol %) and hexanethiol (3% mol/mol of PEGMA). 2% mol of AlBN were dissolved in 0.5 ml of toluene and added to the monomers solution. The mixture was heated at 80° C. for 8 h. After cooling, the polymer was washed twice with acetone and then distilled water.

Hydrogel discs (4 mm thickness and 10 mm diameter) were placed in glass vial containing 10 ml of NaOH 0.1 N until total degradation (absence of visible residue).

A series of gels have been synthesised with increasing amount of naphthyl groups (Table 6).

TABLE 6

Resorbable hydrogels containing naphtyl groups

| | Crosslinker $PEG_{22}$-$PLGA_{12}$ (% mol) | PEG300MA (% mol) | MDO (% mol) | NaphtylMA | Degradation time[a] |
|---|---|---|---|---|---|
| G#11 | 5 | 95 | 5 | 0 | 10 min |
| G#12 | 5 | 85 | 5 | 10 | 1 hour |
| G#13 | 5 | 75 | 5 | 20 | 3 hours |

[a]in NaOH 0.1N

Addition of a cyclic monomer having an exo methylene group thus does not prevent the polymerization of the naphtyl methacrylate at different percentages. The addition of naphtyl MA slowed down the degradation time.

Example 10

Synthesis of Resorbable Microspheres Containing Benzyl Groups MS#17, MS#18, MS#19, MS#20

A 0.5% of aqueous solution of 88% hydrolyzed polyvinylalcohol (120 ml) containing 3% NaCl was introduced into a 250 ml reactor and allowed to stand under a nitrogen atmosphere for 15 min. The monomer phase containing benzyl methacrylate (10 mol %), poly(ethylene glycol) methyl ether methacrylate Mw 300 (80 mol %), 2-methylene-1,3-dioxepane (5 mol %), $PEG_{22}$-$PLGA_{12}$ cross-linker (5 mol %), hexanethiol (3% mol/mol of PEGMA) and 1 mol % AlBN solubilized in 7.5 ml of toluene was degassed by bubbling nitrogen through the solution for 15 min. The monomer phase was added to the aqueous phase at 80° C. and stirred for 8 h. The mixture was filtered hot and washed with acetone and water. Then, beads were freeze-dried.

1 ml of microspheres placed in glass vial containing 10 ml of NaOH 0.1N were totally degraded (absence of visible residue) in 2 min.

Addition of a cyclic monomer having an exo methylene group thus does not prevent the suspension polymerization of the benzyl methacrylate at different percentages.

Example 11

Doxorubicin Loading on Ionic Resorbable Microspheres

A volume of 0.1 mL of sediment microspheres described in example 6 (n=3) were incubated 1 h at RT, under agitation with 3.5 mg of doxorubicin (Pfizer) (conc=2.5 mg/ml) hydrated in water at pH7. Doxorubicin remaining in supernatant was dosed (DO 492 nm) and the loaded dose was calculated by subtraction. Then, loaded microspheres were incubated in 10 mL TRIS buffer (pH 7.3). At 2 min, 10 min, 1 h and 3 h, 1 ml of the release medium was sampled and renewed with fresh TRIS buffer. Doxorubicin in supernatant was dosed (DO 492 nm) and the released dose was calculated (Table 7).

TABLE 7

Doxorubicin releasing from ionic microspheres in TRIS buffer

| Product | Size (μm) | % of loaded drug | % of released drug at 2 min | % of released drug at 10 min | % of released drug at 1 h | % of released drug at 3 h |
|---|---|---|---|---|---|---|
| MS#12 | 300-500 | 94 ± 1% | 20 ± 1% | 41 ± 2% | 78 ± 2% | 82 ± 1% |
| MS#13 | 300-500 | 88 ± 11% | 26 ± 2% | 49 ± 6% | 73 ± 8% | 75 ± 9% |

The addition of an ionic compound allowed high rates of doxorubicin loading by the resorbable microspheres, reaching about 90%, a rate similar to the one of DC beads (BiocompatiblesUK-BTG group).

Example 12

Doxorubicin Loading on Crown Ether Hydrogels 1 mL of doxorubicin solution (0.5 mg/mL) was added to 100 mg of wet gels described in example 8 (n=2). Drug loading was performed overnight at room temperature under mild shaking. The drug loading efficacy was determined by measuring the amount of drug remaining in the supernatant (OD 492 nm). The efficacy of drug loading was expressed as μg of doxurubicin adsorbed per 100 mg of gel. Then, loaded gels were incubated at 37° C. under shaking in 5 mL Tris-HCl buffer, 0.9% NaCl (pH 7.3). After 72 h, free doxorubicin in supernatant was determined (DO 492 nm) and values were calculated for 100 mg of gel (Table 8).

TABLE 8

Doxorubicin loading on resorbable hydrogels containing crown ether

| | Crosslinker PEG$_{22}$-PLGA$_{12}$ (% mol) | PEG300MA (% mol) | MDO (% mol) | Crown ether (% mol) | Loading (μg/100 mg gel) | Release at 72 h (μg/100 mg gel) |
|---|---|---|---|---|---|---|
| G#2 | 5 | 95 | 5 | 0 | 10 +/− 8 | 8.9 ± 0.36 |
| G#9 | 5 | 65 | 5 | 30 | 81 +/− 5 | 50 ± 1.7 |
| G#10 | 5 | 45 | 5 | 50 | 450 +/− 44 | 113 ± 23.8 |

Compared to control, gels incorporating crown ether lead to a doxorubicin loading which increases with the amount of crown-ether. The release was sustained: after 3 days of incubation in saline buffer, the doxorubicin release was still not achieved (only 25 to 30% of drug released). Presence of MDO in the polymer network is compatible with the loading/release of doxorubicin.

Example 13

Ibuprofen/Amphotericin B Nanoparticles Loading on Resorbable Microspheres

Ibuprofen loaded nanoparticles (NP) were prepared by emulsification/solvent evaporation techniques. Typically, 9 mg of PEG-b-PLGA copolymer (Resomer® d5055) and various amount of ibuprofen were dissolved in 1 mL of acetone, and the solution was poured into 9 mL of distilled water. The emulsion thus obtained was gently stirred for 2 h on a magnetic stirrer, in an open vial, in order to evaporate the organic solvent. Nanoparticles thus obtained were collected by centrifugation (11 600 g, 30 min) and washed twice with water.

Amphotericin B loaded nanoparticles were prepared as followed: 9 mg of PEG-b-PLGA copolymer and 563 μg of amphotericin were dissolved into DMSO, and the solution was poured into 9 mL of distilled water. After 1 h of gentle stirring using a magnetic stirred, suspension was dialysed against water for 4 h (MWCO 25000 kDa). Drug loading contents and efficiency were determined by dissolving lyophilized nanoparticles in acetonitrile (for ibuprofen) or DMSO (for amphotericin B) and measuring the amount of drug spectrophotometrically at 264 nm (for ibuprofen) and 421 nm (for amphotericin B) (Table 9).

TABLE 9

Ibuprofen/Amphotericin B loading into nanoparticles

| | $D_H$ (nm) | Pdi | Loading content (%) | Loading efficiency (%) | NP loading on MS | NP release from MS |
|---|---|---|---|---|---|---|
| Bland NP | 98 | 0.26 | | | Yes | >24 h |
| Ibuprofen loaded NP | 96 | 0.16 | 17.6 | 94 | Yes | >24 h |
| Amphotericin B loaded NP | 101 | 0.1 | 6.2 | 99 | yes | >24 h |

To incorporate nanoparticles into microspheres, 100 μL of nanoparticles suspensions were added to 100 μL of lyophilized MS#6. After 8 h of incubation under mechanical stirring at room temperature, nanoparticles loaded MS were washed twice with double distilled water. Then, 1 mL of PBS (10 mM) was added to the suspension of MS. At different time intervals, samples were taken from the supernatant and replaced with the same volume (1 mL) of fresh buffer solution. In these samples, nanoparticles presence was evidenced spectrophotometrically at 260 nm.

For the three kinds of nanoparticles, nanoparticles release was observed during 24 hrs of incubation in buffer. Presence of MDO in the polymer network of the microsphere is compatible with the loading/release of nanoparticles.

Example 14

Indomethacin Loading on Resorbable Benzyl Microspheres

A volume of 0.1 mL of microsphere sediment described in example 10 (n=5) with increasing amount of benzyl groups (0%, 10%, 20%, 30%) were incubated 3 h and 24 h, at RT under agitation with 5 mg of Indomethacin (INDO, Sigma) in solution in DMSO (20 mg/ml) and in phosphate buffer saline.

Indomethacin remaining in supernatant was dosed (OD 260 nm) and the loaded dose was calculated by subtraction (Table 10).

TABLE 10

Indomethacin loading on benzyl microspheres

| Product | Size (μm) | Benzyl | Loaded INDO at 3 h (mg/ml MS) | Loaded INDO at 24 h (mg/ml MS) |
|---|---|---|---|---|
| MS#17 | 300-500 | 0% | 12.9 ± 2.3 | 15.2 ± 1.0 |
| MS#18 | 300-500 | 10% | 20.9 ± 1.4 | 21.0 ± 2.0 |
| MS#19 | 300-500 | 20% | 23.9 ± 0.5 | 25.1 ± 1.9 |
| MS#20 | 300-500 | 30% | 25.8 ± 1.2 | 32.2 ± 1.9 |
|  |  |  | P < 0.001 (Kruskall-Wallis) | P < 0.001 (Kruskall-Wallis) |

Incorporation of benzyl-methacrylate in the microspheres significantly increased the loading capacity of indomethacin by π interactions. Presence of MDO in the polymer network is compatible with the loading of indomethacin.

Example 15

Indomethacin Loading on Resorbable Naphtyl Gels 100 mg gels (hydrated) described in example 9 with increasing amount of naphtyl groups (0%, 10%, 20%) were incubated 3 h and 24 h at RT under agitation with 5 mg of Indomethacin (INDO, Sigma) in solution in DMSO (20 mg/ml) and in phosphate buffer saline.

Indomethacin remaining in supernatant was dosed (DO 260 nm) and the loaded dose was calculated by subtraction (Table 11).

TABLE 11

Indomethacin loading on naphtyl gels

| Product | Naphtyl | Loaded INDO at 3 h (mg/100 mg gel) | Loaded INDO at 24 h (mg/100 mg gel) |
|---|---|---|---|
| G#11 | 0% | 1.0 ± 0.2 | 1.2 ± 0.1 |
| G#12 | 10% | 0.9 ± 0.0 | 1.5 ± 0.2 |
| G#13 | 20% | 1.8 ± 0.5 | 2.7 ± 0.3 |

P = 0.0219 at 3 h, and
P = 0.0105 (KW) at 24 h.

Incorporation of naphtyl-methacrylate in the hydrogels significantly increased the loading capacity of indomethacin by π interactions. Presence of MDO in the polymer network is compatible with the loading of indomethacin.

Example 16

In Vitro Cytotoxicity Analysis

Cytotoxicity of microspheres was analyzed using extracts of microspheres prepared in cell culture medium. Briefly, mouse fibroblasts (L929) cultures were maintained in high-glucose DMEM medium with 10% FBS, 2 mM L-glutamine, 50 μg/mL streptomycin, 50 Units/mL penicillin in CO2 incubator at 37° C. L929 cells harvesting was performed using Trypsin EDTA (Lonza) and subcultures started in 96 well plates (NUNC) at densities of $5 \cdot 10^3$ cells/well. Microspheres extracts were prepared in sterile tubes, 500 μL of microspheres pellet in DMEM were added and the volume was completed to 3 mL with cell culture medium. Samples were incubated at 37° C. under agitation up to complete degradation of microspheres. The concentration of material was around 25 mg/mL in the microsphere extracts. Chirurgical glove fragments (latex) were used as positive control of cytotoxicity. The day after cell seeding, the microspheres extracts in cell culture medium were completed with bovine serum and the pH was adjusted (around pH 7) before addition to non-confluent fibroblasts (6 to 8 wells/condition). Extracts obtained with chirurgical gloves were also added to mouse fibroblasts. After 72 h of culture (37° C., 5% $CO_2$), medium was removed, cells were washed with 100 μL of PBS, before addition of 100 μL bicinchoninic acid solution (BCA protein Reagent, Sigma) containing 0.08% CuSO4 (w/v) and 0.05% Triton X-100. After incubation (1 h at 37° C.), absorbance was measured at 570 nm and the amount of proteins was obtained by extrapolation from standard curve using bovine serum albumin. (Table 12).

TABLE 12

Cytotoxicity of resorbable microspheres

| Code | Crosslinker (% mol) | MDO (% mol) | Co-Monomer (% mol) | L929 total cell proteins (% of control) | Cytotoxic status |
|---|---|---|---|---|---|
| Cell culture medium | — | — | — | 100 | — |
| Latex[a] | — | — | — | 22.73 +/− 5.74 | cytotoxic |
| MS#2 | $PEG_{13}PLGA_{12}$ (5%) | 0 | — | 71.36 +/− 6.14 *p = 0.0003 | Non-cytotoxic |
| MS#3 | $PEG_{13}PLA_{12}$ (5%) | 0 | — | 83.80 +/− 3.99 *p = 0.0003 | Non-cytotoxic |

TABLE 12-continued

Cytotoxicity of resorbable microspheres

| Code | Crosslinker (% mol) | MDO (% mol) | Co-Monomer (% mol) | L929 total cell proteins (% of control) | Cytotoxic status |
|---|---|---|---|---|---|
| MS#4 | PEG$_{22}$PLGA$_{12}$ (5%) | 0 | — | 85.09 +/− 4.5 *p = 0.0003 | Non-cytotoxic |
| MS#10 | PEG$_{13}$-PLGA$_{12}$ (5%) | 0 | β-Carboxy ethyl acrylate (10%) | 61.59 +/− 7.7 *p = 0.0008 | Mildly-cytotoxic |
| MS#12 | PEG$_{13}$-PLA$_{12}$ (5%) | 0 | Methacrylic acid (10%) | 74.94 +/− 7.04 *p = 0.0003 | Non-cytotoxic |
| MS#13 | PEG$_{13}$-PLGA$_{12}$ (5%) | 0 | Methacrylic acid (10%) | 72.34 +/− 4.26 *p = 0.0003 | Non-cytotoxic |
| MS#5 | PEG$_{22}$PLGA$_{12}$ (5%) | 2.5 | — | 77.57 +/− 3.74 *p = 0.0062 | Non-cytotoxic |
| MS#6 | PEG$_{22}$PLGA$_{12}$ (5%) | 5 | — | 86.31 +/− 4.44 *p = 0.0039 | Non-cytotoxic |
| MS#7 | PEG$_{22}$PLGA$_{12}$ (5%) | 10 | — | 88.46 +/− 7.67 *p = 0.0007 | Non-cytotoxic |
| MS#9 | PEG$_{22}$PLGA$_{12}$ (5%) | 30 | — | 73.65 +/− 5.16 *p = 0.0039 | Non-cytotoxic |
| MS#16 | PEG$_{22}$-PLGA$_{12}$ (5%) | 5 | Methacrylic acid (50%) | 22.79 +/− 3.32 *p = 0.0039 | Cytotoxic |
| MS#18 | PEG$_{22}$PLGA$_{12}$ (5%) | 5 | Benzyl methacrylate (10%) | 86.96 +/− 3.81 *p = 0.0039 | Non-cytotoxic |

[a]Cytotoxic control
*comparisons between microspheres and Latex were performed according to non-parametric Mann-Whitney test. Significance was set at p < 0.05.

Culture of cells for 3 days with microsphere extracts did not induce cell death as observed with latex control (p<0.05). Significant cytotoxicity was defined as an effect leading to an inhibition of cell growth of more than 30% as compared to the control cultures (Lin et al 2009 Colloid Surface B, 70: 132-41).

Methacrylic acid at 10% mol (MS#12 and MS#13) in resorbable microspheres was not cytotoxic in comparison with microspheres prepared without methacrylic acid (MS#3 and MS#2). At the opposite, incorporation of a high content of methacrylic acid (50% mol) within microsphere (MS#16) generated toxicity, attributable to a quick resorption giving a high release of protons (pH dropped below 7) which compromised the cell survival. Addition of β-Carboxy-ethyl acrylate (10% mol) in microspheres (MS#10) induced a mild toxicity; the growth inhibition was however close to the threshold value for cytotoxicity (70%). Methacrylic acid seems to be a better anionic co-monomer compared to β-carboxy-ethyl acrylate for preparation of anionic microspheres in regard to the toxicity results.

Addition of a hydrophobic co-monomer (benzyl methacrylate, 10% mol) in microspheres containing MDO (5% mol) did not arrest cell proliferation.

Except for (MS#10 and MS#16), all proliferation values of the resorbable microspheres listed in table 12 (in presence or not of MDO) were higher than 70%, thus they were non-cytotoxic towards cultured cells.

Example 17

Subcutaneous Implantation in Rabbit

White New Zealand rabbits (n=22) were implanted in the back skin with resorbable microspheres (total amount of 0.8 mL of microsphere sediment per rabbit) in saline or with saline only (SHAM). Rabbits were than sacrificed at day 2, day 7 or day 28, according to the Table 13. Rapidly resorbable microspheres (resorption <24 h in vitro) were evaluated only at D2, and D7. Slower resorbable microspheres (resorption >4 days in vitro) were evaluated at D7 and D28. Tissue reaction and material resorption were assessed by histology. Main organs were harvested at sacrifice and checked for abnormalities suggesting a systemic toxicity.

TABLE 13

| Product | Size (μm) | Cross-linker | Methacrylic acid | Number of rabbits at D2 | Number of rabbits at D7 | Number of rabbits at D28 |
|---|---|---|---|---|---|---|
| MS#1 | 700-900 | PEG$_{13}$-PLGA$_{12}$ | 0% | | N = 2 | |
| MS#3 | 300-500 | PEG$_{13}$-PLA$_{12}$ | 0% | — | N = 2 | N = 2 |
| MS#12 | 300-500 | PEG$_{13}$-PLA$_{12}$ | 10% | — | N = 2 | N = 2 |
| MS#2 | 300-500 | PEG$_{13}$-PLGA$_{12}$ | 0% | N = 2 | N = 2 | — |
| MS#13 | 300-500 | PEG$_{13}$-PLGA$_{12}$ | 10% | N = 2 | N = 2 | — |
| SHAM | | Saline only | | N = 2 | N = 2 | N = 2 |

Results

All microspheres triggered only a mild inflammatory reaction, involving some neutrophils at D2, and macrophages at D7 and D28.

PLA-based microspheres at D7 conserved there shape, and were at an advanced stage of resorption, being replaced by fibrin, and being colonized with fibroblast-like cells.

PLA-based microspheres at D28 were not visible anymore, totally resorbed. The cavity of implantation was filled with fibroblasts and young collagen fibers, and only few remnant macrophages.

PLGA-based microspheres at D2 conserved there shape and were at an advanced stage of resorption, being replaced by fibrin, with no cell colonization.

PLGA-based microspheres at D7 were not visible anymore in a flattened cavity, totally resorbed, with only a small scar tissue at the site of implantation, with few remnant macrophages.

No systemic toxic effects were detected in draining lymph nodes, livers, kidney, heart, and spleen of rabbits implanted with resorbable microspheres (no difference with SHAM).

Example 18

Embolization with Resorbable Microspheres

Resorbable microspheres (MS#13) were used for embolization in different animal models to assess their ability to occlude an arterial network (Table 14).

TABLE 14

| Animal model for embolization | Number of animals | Nature of the microspheres | Size (μm) | Size of micro-catheter | Results |
|---|---|---|---|---|---|
| Uterine arteries in hormonally cycled ewe | 1 | MS#13 $PEG_{13}$-$PLGA_{12}$, 10% MA | 500-800 | 2.7 F | Initial complete embolization. Full recanalization of uterine arteries at D7. No ischemic or haemorragheic lesions of the uterus. |
| Renal arteries in minipig | 10 | MS#13 $PEG_{13}$-$PLGA_{12}$, 10% MA | 300-500 700-900 | 2.4 F 4 F | Selective occlusion of the interlobular arteries of the lower pole. Complete angiographic recanalization at D7 Selective occlusion of the proximal interlobar arteries of the lower pole. Complete angiographic recanalization at D7 No microsphere visible in pathology at D7 for the two sizes |
| sHepatic arteries and VX2 tumor in rabbit | 4 | MS#13 $PEG_{13}$-$PLGA_{12}$, 10% MA | 100-300 300-500 | 2.1 F | Doxorubicin loaded microspheres were found in histology in tumor nodules and induced tumor necrosis. |

Pig Kidney Recanalization
Materials & Methods

Minipigs underwent a selective embolization of the lower pole of kidney with 300-500 μm microspheres injected intraarterially through a 2.4 F microcatheter, until disappearance of the parenchyma opacification in the targeted area. One week after the procedure, a control angiogram was performed and recanalization of the renal arteries was evaluated. On angiograms, the area of staining by contrast medium was measured immediately after embolization, and after 1 week, and compared (percentage) to the area of staining of the renal arteries before embolization.

Results

The lower poles of kidneys were successfully embolized with resorbable microspheres. Injectability of the microspheres was easy, like the injection of water.

Arteries up to 1 mm of diameter were occluded in the lower pole. At sacrifice, the renal arteries were recanalized up to the cortical area. At D0 and at W1, the vascularization percentages were respectively 76% and 93% compared to initial angiogram (100%), which proved a quite complete recanalization of renal arteries.

The invention claimed is:

1. A cross linked polymer obtainable from the polymerization of:

(i) at least one monomer of formula (I)

$$(CH_2\!\!=\!\!CR_1)CO\!-\!K \qquad (I)$$

wherein:

K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;

$R_1$, $R_2$, $R_3$, $R_4$ and $R_5$ independently represent H or a C1-C6 alkyl;

(ii) at least between 0.1 and 50% mol of a cyclic monomer having an exo-methylene group of formula (II):

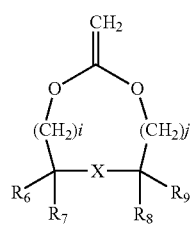

(II)

wherein:

$R_6$, $R_7$, $R_8$, and $R_9$ represent independently H or a $C_5$-$C_7$ aryl group or $R_6$ and $R_9$ are absent and $R_7$ and $R_8$ form together with the carbon atom on which they are bonded a $C_5$-$C_7$ aryl group;

i and j represent independently an integer chosen between 0 and 2;

X represents either O or X is not present and in this latter case, $CR_6R_7$ and $CR_8R_9$ are linked via a single bond C—C and (iii) at least one bio-resorbable block copolymer cross-linker wherein the bio-resorbable block copolymer cross-linker is of the following formula (III):

$$(CH_2=CR_{11})CO-(X_n)_l-PEG_p-Y_k-CO-(CR_{12}=CH_2) \quad (III)$$

wherein:

$R_{11}$ and $R_{12}$ independently represent H or a C1-C6 alkyl;

X and Y independently represent PLA, PGA, PLGA or PCL;

n, p, and k respectively represent the degree of polymerization of X, PEG, and Y, n and k independently being integers from 1 to 150, and p being an integer from 1 to 100; and l represents 0 or 1.

2. The polymer of claim 1, wherein the bio-resorbable block copolymer cross-linker is of a formula selected from the group consisting of:

$$(CH_2=CR_{11})CO-PLA_n-PEG_p-PLA_k-CO-(CR_{12}=CH_2),$$

$$(CH_2=CR_{11})CO-PGA_n-PEG_p-PGA_k-CO-(CR_{12}=CH_2),$$

$$(CH_2=CR_{11})CO-PLGA_n-PEG_p-PLGA_k-CO-(CR_{12}=CH_2),$$

$$(CH_2=CR_{11})CO-PCL_n-PEG_p-PCL_k-CO-(CR_{12}=CH_2),$$

$$(CH_2=CR_{11})CO-PEG_p-PLA_k-CO-(CR_{12}=CH_2),$$

$$(CH_2=CR_{11})CO-PEG_p-PGA_k-CO-(CR_{12}=CH_2),$$

$$(CH_2=CR_{11})CO-PEG_p-PLGA_k-CO-(CR_{12}=CH_2);$$ and $$(CH_2=CR_{11})CO-PEG_p-PCL_k-CO-(CR_{12}=CH_2);$$

wherein $R_{11}$, $R_{12}$, n, p and k are as defined in claim 1.

3. The polymer of claim 1, wherein the monomer of formula (I) is selected from the group consisting of sec-butyl acrylate, n-butyl acrylate, t-butyl acrylate, t-butyl methacrylate, methylmethacrylate, N-dimethyl-aminoethyl(methyl)acrylate, N,N-dimethylaminopropyl-(meth)acrylate, t-butylaminoethyl (methyl)acrylate, N,N-diethylaminoacrylate, acrylate terminated poly(ethylene oxide), methacrylate terminated poly(ethylene oxide), methoxy poly(ethylene oxide) methacrylate, butoxy poly(ethylene oxide) methacrylate, acrylate terminated poly(ethylene glycol), methacrylate terminated poly(ethylene glycol), methoxy poly(ethylene glycol) methacrylate, butoxy poly(ethylene glycol) methacrylate, poly(ethylene glycol) methyl ether methacrylate.

4. The polymer of claim 1, wherein the cyclic monomer of formula (II) is selected from the group consisting of 2-methylene-1,3-dioxolane, 2-methylene-1,3-dioxane, 2-methylene-4-phenyl-1,3-dioxolane, 2-methylene-1,3-dioxepane, 5,6-benzo-2-methylene-1,3-dioxepane and 2-methylene-1,3,6-Trioxocane.

5. The polymer of claim 1, obtainable from the polymerization of the at least one monomer of formula (I), the at least one cyclic monomer of formula (II), the at least one bio-resorbable block copolymer cross-linker, and further at least one chain transfer agent which is advantageously a cycloaliphatic or an aliphatic thiol typically having from 2 to about 24 carbon atoms, and optionally having a further functional group selected from the groups amino, hydroxy and carboxy.

6. The polymer of claim 5, obtainable from the polymerization of the at least one monomer, the at least one cyclic monomer, the at least one bio-resorbable block copolymer cross-linker, optionally at least one chain transfer agent as defined in claim 5, and at least one further monomer selected from the list comprising:

(i) a drug-carrying monomer of the following formula (IV):

$$(CH_2=CR_{13})CO-L_1-D \quad (IV)$$

wherein:

$R_{13}$ represents H or a $C_1$-$C_6$ alkyl;

$L_1$ represents a linker moiety having from 1 to 20 carbon atoms comprising a hydrolyzable function linked to the D group;

the D group represents a drug or a prodrug; and (ii) a charged, ionisable, hydrophilic, or hydrophobic monomer of the following formula (V):

$$(CH_2=CR_{14})CO-M-E \quad (V)$$

wherein:

$R_{14}$ represents H or a $C_1$-$C_6$ alkyl;

M represents a single bond or a linker moiety having from 1 to 20 carbon atoms;

E represents a charged, ionisable, hydrophilic, or hydrophobic group having 100 atoms at the most.

7. The polymer of claim 6, wherein E is selected from the group constituted of COOH, COO$^{31}$, SO$_3$H, SO$_3$$^{31}$, PO$_4$H$_2$, PO$_4$$^{2-}$, NR$_{15}$R$_{16}$, NR$_{15}$R$_{16}$R$_{17}$$^+$, in which $R_{15}$, $R_{16}$ and $R_{17}$ independently represent H or a $C_1$-$C_6$ alkyl, a $C_1$-$C_{20}$ alkyl group, a $C_5$-$C_{20}$ aryl group, a (5-30-members) heteroaryl group containing an heteroatom chosen in the group consisting of O, N or S, a O—$C_5$-$C_{20}$ aryl group, a O-(5-30-members) heteroaryl group, a crown ether and a cyclodextrin.

8. The polymer of claim 6, obtainable from the polymerization of the at least one monomer, the at least one cyclic monomer, the at least one bio-resorbable block copolymer cross-linker, the at least one drug-carrying monomer, optionally the at least one charged, ionisable, hydrophilic, or hydrophobic monomer, and at least one hydrophilic monomer of the following formula (IX):

$$(CH_2=CR_{23})CO-Q \quad (IX)$$

wherein:

$R_{23}$ represents H or a $C_1$-$C_6$ alkyl;

Q represents a $C_1$-$C_{100}$ alkyl optionally substituted by at least one substituent selected from the group consisting of an hydroxyl, an oxo or an amino function.

9. The polymer claim 6, loaded with a drug or a prodrug or a diagnostic agent.

10. The polymer of claim 9, wherein the drug or the prodrug is chosen in the group consisting of anti-inflammatory agents, local anesthetics, analgesics, antibiotics, anticancer agents, tissue regeneration agents, oligosaccharides advantageously having a degree of polymerization (DP) of 3 to 10, steroid, and mixture thereof.

11. The polymer of claim 9, wherein the drug is in the form of nanoparticles loaded with the drug with an average size lower than 1 μm, the nanoparticles being nanospheres or nanocapsules.

12. The polymer claim 1, which is in the form of a film, a foam, a particle, a lump, a thread, or a sponge.

13. A pharmaceutical composition comprising at least one polymer of claim 1, in association with a pharmaceutically acceptable carrier.

14. An injectable pharmaceutical composition comprising (a) a polymer of claim 1, having a spherical shape of a diameter of between 50 and 500 μm and a resorption time of between 2 days to 3 weeks;

(b) a polymer of claim 1 having a spherical shape of a diameter of between 50 and 500 μm and a resorption time of between one to 3 months; and (c) at least a pharmaceutically acceptable excipient.

15. The composition of claim 14 wherein the spherical particles of polymer (a) and (b) do not have the same diameter, advantageously the diameter of the spherical particles of polymer (a) is of between 100 and 300 μm and the diameter of the spherical particles of polymer (b) is of between 300 and 500 μm.

16. Implant containing the polymer of claim 1.

17. The implant of claim 16, for implantation into tissues, internal anatomical spaces, body cavities, ducts and vessels, advantageously in facial tissue.

18. Method for filling of and/or camouflaging and/or correcting wrinkles, fine lines, skin cracks, cutaneous depressions, lipodystrophies, facial hemiatrophy, second branchial arch syndrome and/or scars, in particular acne scars and/or smoothing out irregularity of the skin and/or as a matrix for cellular culture and/or for tissue engineering, comprising the the polymer of claim 1 to a subject in need thereof.

19. A method for correcting skin ageing and/or for wound healing and/or for tissular reconstruction and/or for soft tissue repair, and/or for treating inflammation, cancer, arteriovenous malformations, cerebral aneurysm, gastrointestinal bleeding, epistaxis, primary post-partum haemorrhage and/or surgical haemorrhage and/or for regenerating tissue in human or animal, comprising administering a therapeutically effective amount of the polymer of claim 1.

* * * * *